United States Patent
Nazhat et al.

(10) Patent No.: US 10,507,263 B2
(45) Date of Patent: Dec. 17, 2019

(54) BORATE-GLASS BIOMATERIALS

(71) Applicant: THE ROYAL INSTITUTION FOR THE ADVANCEMENT OF LEARNING/McGILL UNIVERSITY, Montreal (CA)

(72) Inventors: Showan Nazhat, Montreal (CA); William Cole Lepry, Montreal (CA)

(73) Assignee: THE ROYAL INSTITUTION FOR THE ADVANCEMENT OF LEARNING/MCGILL UNIVERSITY, Montreal (CA)

( * ) Notice: Subject to any disclaimer, the term of this patent is extended or adjusted under 35 U.S.C. 154(b) by 0 days.

(21) Appl. No.: 15/317,746

(22) PCT Filed: Jun. 9, 2015

(86) PCT No.: PCT/CA2015/000365
§ 371 (c)(1),
(2) Date: Dec. 9, 2016

(87) PCT Pub. No.: WO2015/188252
PCT Pub. Date: Dec. 17, 2015

(65) Prior Publication Data
US 2017/0274118 A1 Sep. 28, 2017

Related U.S. Application Data

(60) Provisional application No. 62/163,630, filed on May 19, 2015, provisional application No. 62/006,472, filed on Jun. 9, 2014.

(51) Int. Cl.
| | | |
|---|---|---|
| A61K 8/19 | (2006.01) |
| A61K 8/24 | (2006.01) |
| A61K 33/00 | (2006.01) |
| A61L 27/10 | (2006.01) |
| A61L 27/32 | (2006.01) |
| A61L 31/02 | (2006.01) |
| C03C 1/00 | (2006.01) |
| A61L 27/54 | (2006.01) |
| A61L 27/16 | (2006.01) |
| A61L 27/52 | (2006.01) |
| A61K 8/81 | (2006.01) |
| A61Q 19/00 | (2006.01) |
| C03C 8/08 | (2006.01) |
| C03C 8/14 | (2006.01) |
| C03C 4/00 | (2006.01) |
| C03C 3/097 | (2006.01) |
| C03C 10/00 | (2006.01) |
| C03C 11/00 | (2006.01) |

(52) U.S. Cl.
CPC ............... A61L 27/10 (2013.01); A61K 8/19 (2013.01); A61K 8/24 (2013.01); A61K 8/8152 (2013.01); A61L 27/16 (2013.01); A61L 27/32 (2013.01); A61L 27/52 (2013.01); A61L 27/54 (2013.01); A61Q 19/00 (2013.01); C03C 1/006 (2013.01); C03C 3/097 (2013.01); C03C 4/0014 (2013.01); C03C 8/08 (2013.01); C03C 8/14 (2013.01); C03C 10/0054 (2013.01); C03C 11/007 (2013.01); A61K 2800/70 (2013.01); A61L 2300/412 (2013.01); A61L 2420/06 (2013.01); A61L 2430/02 (2013.01); A61L 2430/34 (2013.01)

(58) Field of Classification Search
None
See application file for complete search history.

(56) References Cited

U.S. PATENT DOCUMENTS

| | | | |
|---|---|---|---|
| 4,786,555 A * | 11/1988 | Howard, Jr. | ............ A61L 27/12 428/403 |
| 6,010,713 A | 1/2000 | Zhong et al. | |
| 6,709,744 B1 | 3/2004 | Day et al. | |
| 7,758,803 B2 | 7/2010 | Chang | |
| 8,173,154 B2 | 5/2012 | Jung et al. | |
| 8,287,896 B2 | 10/2012 | Jung et al. | |
| 8,449,904 B1 | 5/2013 | Jung | |
| 8,821,919 B2 | 9/2014 | Jung | |
| 9,402,724 B2 | 8/2016 | Day et al. | |
| 9,456,890 B2 | 10/2016 | Day et al. | |
| 9,486,554 B2 | 11/2016 | Jung et al. | |
| 9,498,459 B2 | 11/2016 | Pomrink et al. | |
| 9,561,303 B2 | 2/2017 | Jung et al. | |
| 2014/0079789 A1 | 3/2014 | Pomrink et al. | |

(Continued)

FOREIGN PATENT DOCUMENTS

| | | |
|---|---|---|
| CN | 104334503 B | 2/2015 |
| WO | 2014159240 A1 | 10/2014 |

(Continued)

OTHER PUBLICATIONS

Huang et al. (J Mater Sci: Mater Med (2006) 17:583-596).*
Sepulveda et al. (J Biomed Mater Res (Appl Biomater) 58: 734-740, 2001).*
Sepulveda et al. (J Biomed Mater Res 61: 301-311, 2002.).*
Bengisu et al. (J Sol-Gel Sci Technol (2008) 45:237-243).*
Xiao et al. (Journal of Materials Research. Dec. 2012, vol. 27, Issue 24, 3147-3156).*
Ouis, M. A et al., "Corrosion mechanism and bioactivity of borate glasses analogue to Hench's bioglass", Processing and Application of Ceramics, 2012, vol. 6, No. 3, pp. 141-149.
Han, X. et al., "Reaction of sodium calcium borate glasses to form hydroxyapatite", Journal of Materials Science: Materials in Medicine, 2007, vol. 18, No. 9, pp. 1837-1847.
Gu, Y. et al., "Kinetics and mechanisms of converting bioactive borate glasses to hydroxyapatite in aqueous phosphate solution", Journal of Materials Science, 2011, vol. 46, No. 1, pp. 47-54.
Abdelghany, A M. et al., "Bone bonding ability behaviour of some ternary borate glasses by immersion in sodium phosphate solution", Ceramics International, 2012, vol. 38, pp. 1105-1113.

(Continued)

Primary Examiner — Abigail Vanhorn
(74) Attorney, Agent, or Firm — BCF LLP

(57) ABSTRACT

Borate-glass biomaterials comprising: $aNa_2O \cdot bCaO \cdot cP_2O_5 \cdot dB_2O_3$ wherein a is from about 1-40 wt %, b is from about 10-40 wt %, c is from about 1-40 wt %, and d is from about 35-80 wt %; and wherein the biomaterial has a surface area per mass of more than about 5 $m^2/g$. Methods of making and uses of these biomaterials.

27 Claims, 13 Drawing Sheets

(56) References Cited

U.S. PATENT DOCUMENTS

| | | |
|---|---|---|
| 2015/0079146 A1 | 3/2015 | Pomrink et al. |
| 2015/0283300 A1 | 10/2015 | Pomrink et al. |
| 2015/0352247 A1 | 12/2015 | Jie et al. |
| 2016/0051723 A1 | 2/2016 | Pomrink et al. |
| 2016/0318992 A1 | 11/2016 | Pomrink et al. |
| 2017/0056553 A1 | 3/2017 | Pomrink et al. |
| 2017/0342382 A1 | 11/2017 | Deng et al. |
| 2017/0349876 A1 | 12/2017 | Deng et al. |

FOREIGN PATENT DOCUMENTS

| | | |
|---|---|---|
| WO | 2015137981 A1 | 9/2015 |
| WO | 2016040481 A1 | 3/2016 |

OTHER PUBLICATIONS

International Search Report with regard to PCT/CA2015/000365 dated Aug. 27, 2015.
"Wound healing borate glass nanofibers", American Ceramic Society Bulletin, 2011, vol. 90, No. 4, pp. 1-56.
Carta et al., "The effect of composition on the structure of sodium borophosphate glasses", Journal of Non-Crystalline Solids, 2008, No. 354, pp. 3671-3677.
Carta et al., "Sol-gel synthesis and structural characterisation of P2O5—B2O3—Na2O glasses for biomedial applications", Journal of Materials Chemistry, 2009, vol. 19, pp. 150-158.
Chryssikos et al., "A structural assessment of glass formation in alkali borates: Melt quenching versus gel drying", Journal of Materials Science Letters, 1995, vol. 14, pp. 268-270.
Irwin et al., "Spectroscopic Investigations of borosiloxane bond formation in the sol-gel process", Journal of Non-Crystalline Solids, 1987, vol. 89, pp. 191-205.
Ivanova et al., Sol-gel synthesis of glasses in the systems B2O3—MnOm (M=Li, Ba, Zn), Physics and Chemistry Glasses, 2000, vol. 41, No. 6, pp. 349-351.
Jung, "Bioactive Borate Glasses", Bio-Glasses: An Introduction, 2012, pp. 76-95.
Kruner et al., "Some properties of N-containing lithium borate glasses prepared by different sol-gel methods", Journal of Non-Crystalline Solids, 1990, vol. 121, pp. 167-170.
Miguez-Pacheco et al., "Bioactive glasses beyond bone and teeth: Emerging applications in contact with soft tissues", Acta Biomaterialia, 2015, vol. 13, pp. 1-15.
Ota et al., "Variation of the gel region with heat-treatment in the B2O3—Na2O—TiO2, system compared with the melt-quenched glass region", Journal of Materials Science, 1990, vol. 25, pp. 4259-4265.
Tohge et al., "Preparation of 20 Na2O 80B2O3 glasses by sol-gel method", Journal of Non-Crystalline Solids, 1984, vol. 68, pp. 411-418.
Weinberg et al., "The preparation and characterization of a lithium borate glass prepared by the gel technique", Journal of Materials Science, 1985, vol. 20, pp. 1501-1508.
Wright, Adrian C. "My Borate Life: An Enigmatic Journey" International Journal of Applied Glass Science, 2015, vol. 6, No. 1, pp. 45-63.
Shelby, James E. "Structures of glasses" Introduction to Glass Science and Technology: Edition 2; 2005, ch. 5, pp. 72-110.
Wright, Adrian C. And Dalba, Giuseppe "Borate versus silicate glasses: why are they so different?" Physics and Chemistry of Glasses: European Journal of Glass Science and Technology, Part B, Oct. 2010 vol. 51, No. 5, pp. 233-254.
Wright, Adrian C. And Dalba, Giuseppe "Borate versus silicate glasses: why are they so different?" Physics and Chemistry of Glasses: European Journal of Glass Science and Technology, Part B, Oct. 2010 vol. 51, No. 5, pp. 255-265.
Marquardt et al. "Effects of borate-based bioactive glass on neuron viability and neurite extension" J Biomed Mater Res Part A 2014, vol. 102A, pp. 2767-2775.
Marzouk et al. "In vitro bioactivity of soda lime borate glasses with substituted SrO in sodium phosphate solution" Processing and Application of Ceramics 8 2014, vol. 3, pp. 167-177.
Ning et al. "Synthesis and in vitro bioactivity of a borate-based bioglass" Materials Letters 2007, vol. 61, 5223-5226.
O'Connell et al."Host responses to a strontium releasing high boron glass using a rabbit bilateral femoral defect model" J Biomed Mater Res Part B 2016, pp. 1-10.
O'Connell et al. "Linear release of strontium ions from high borate glasses via lanthanide/alkali substitutions" Journal of Non-Crystalline Solids 2015, vol. 430, pp. 1-8.
Rahaman et al. "Preparation and bioactive characteristics of porous borate glass substrates" Advances in Bioceramics and Biocomposites, 2005, pp. 3-10.
Simon "Structure and dissolution investigation of calcium-bismuth-borate glasses and vitroceramics containing silver" J Mater Sci: Mater Med 2007, vol. 18, pp. 507-512.
Pan et al. "Strontium borate glass: potential biomaterial for bone regeneration" http://rsif.royalsocietypublishing.org/, doi:10.1098/rsif.2009.0504, 2009, retrieved on Jan. 16, 2018.
Wang et al. "Preparation of hollow hydroxyapatite microspheres" J Mater Sci: Mater Med 2006, vol. 17, pp. 641-646.
Watters et al. "Angiogenic Effect of Bioactive Borate Glass Microfthers and Beads in the Hairless Mouse" Biomed. Glasses 2015; vol., pp. 173-184.
Xiao et al. "Evaluation of Ti implants coated with Ag-containing borate bioactive glass for simultaneous eradication of nfection and fracture fixation in a rabbit tibial model" Materials Research Society 2012, vol. 27, No. 24, pp. 3147-3158.
English Abstract of CN104334503B, retrieved from Espacenet on Mar. 14, 2018.
Li et al. "Antibacterial and osteo-stimulatory effects of a borate-based glass series doped with strontium ions" Journal of Biomaterials Applications, 2016, vol. 31, No. 5, pp. 674-683.
Liang et al. "Bioactive comparison of a borate, phosphate and silicate glass" Journal of Materials Research Society, 2006, vol. 21, No. 1, pp. 125-131.
Kolan et al. "Solvent Based 3D Printing of Biopolymer/Bioactive Glass Composite and Hydrogel for Tissue Engineering Applications" Procedia CIRP, 2017, vol. 65, pp. 38-43.
Xie et al."Treatment of osteomyelitis and repair of bone defect by degradable bioactive borate glass releasing vancomycin" Journal of Controlled Release 2009 vol. 139, pp. 118-126.
Abdelghany et al. "Role of SrO on the bioactivity behavior of some ternary borate glasses and their glass ceramic derivatives" Spectrochimica Acta Part A: Molecular and Biomolecular Spectroscopy, 2016, vol. 152, pp. 126-133.
Abdelghany "Novel method for early investigation of bioactivity in different borate bio-glasses" Spectrochimica Acta Part A: Molecular and Biomolecular Spectroscopy, 2013, vol. 100, pp. 120-126.
Abdelghany et al. "Zinc containing borate glasses and glass-ceramics: Search for biomedical applications" Processing and Application of Ceramics 8, 2014, vol. 4, pp. 185-193.
Bengisu "Borate glasses for scientific and industrial applications: a review" J Mater Sci, 2016, vol. 51, pp. 2199-2242.
Bi et al. "Evaluation of bone regeneration, angiogenesis, and hydroxyapatite conversion in critical-sized rat calvarial defects implanted with bioactive glass scaffolds" J Biomed Mater Res Part A, 2012, vol. 100A, pp. 3267-3275.
Bi et al. "Effect of bioactive borate glass microstructure on bone regeneration, angiogenesis, and hydroxyapatite conversion in a rat calvarial defect model" Acta Biomaterialia, 2013, vol. 9, pp. 8015-8026.
Brown et al. "Effect of borate glass composition on its conversion to hydroxyapatite and on the proliferation of MC3T3-E1 cells", http://onlinelibrary.wiley.com/, 2008, DOI: 10.1002/jbm.a.31679, retrieved on Jan. 16, 2018.
Rahaman et al. "Bioactive glass in tissue engineering" Acta Biomaterialia, Jun. 2011, vol. 7, No. 6, pp. 2355-2373.
Zhao et al. "Wound dressings composed of copper-doped borate bioactive glass microfibers stimulate angiogenesis and heal full-thickness skin defects in a rodent model" Biomaterials 2015, vol. 53, pp. 379-391.

(56) References Cited

OTHER PUBLICATIONS

Zhang et al. "Bioactive borate glass promotes the repair of radius segmental bone defects by enhancing the osteogenic differentiation of BMSCs" Biomed. Mater 2015, vol. 10, pp. 1-10.
Balasubramanian et al. "Boron-containing bioactive glasses in bone and soft tissue engineering" Journal of the European Ceramic Society, 2018, vol. 38, pp. 855-869.
Cui et al. "A novel injectable borate bioactive glass cement for local delivery of vancomycin to cure osteomyelitis and regenerate bone" J Mater Sci: Mater Med, 2014, vol. 25, pp. 733-745.
Deliomanli "Size-dependent degradation and bioactivity of borate bioactive glass" Ceramics International 7, 2013, vol. 39, pp. 8087-8095.
Deliomanli et al. "Evaluation of borate bioactive glass scaffolds with different pore sizes in arat subcutaneous implantation model" Journal of Biomaterials Applications, 2014, vol. 28(5), pp. 643-653.
Deliomanli "Synthesis and characterization of cerium- and gallium-containing borate bioactive glass scaffolds for bone tissue engineering" J Mater Sci: Mater Med, 2015, pp. 26-67.
Ding et al. "A Novel Injectable Borate Bioactive Glass Cement as an Antibiotic Delivery Vehicle for Treating Osteomyelitis" Plos One 9, 2014,vol. 1, e85472. doi:10.1371/joumal.pone.0085472, retrieved on Jan. 16, 2018.
El Batal et al. "Comparative studies on the bioactivity of some borate glasses and glass—ceramics from the two systems:Na2O—CaO—B2O3 and NaF—CaF2—B2O3" Ceramics International, 2016, vol. 42, pp. 8247-8256.
Deliomanli A. M. "In vitro assessment of degradation and mineralisation of V2O5 substituted borate bioactive glass scaffolds" Materials Technology: Advanced Performance Materials, 2014, vol. 29, No. 6,, pp. 358-365.
Fu et al. "In vitro evaluation of borate-based bioactive glass scaffolds prepared by a polymer foam replication method" Materials Science and Engineering, 2009, vol. C 29, pp. 2275-2281.
Fu et al. "Silicate, borosilicate, and borate bioactive glass scaffolds with controllable degradation rate for bone tissue engineering applications. I. Preparation and in vitro degradation" http://onlinelibrary.wiley.com/ DOI: 10.1002/jbm.a.32824, 2010, retrieved on Jan. 16, 2018.
Fu et al. "Silicate, borosilicate, and borate bioactive glass scaffolds with controllable degradation rate for bone tissue engineering applications.II. In vitro and in vivo biological evaluation" http://onlinelibrary.wiley.com/ DOI: 10.1002/jbm.a.32823, 2010, retrieved on Jan. 16, 2018.
Zhang et al. "Evaluation of Injectable Strontium-Containing Borate Bioactive Glass Cement with Enhanced Osteogenic Capacity in a Critical-Sized Rabbit Femoral Condyle Defect Model" Acs Appl. Mater. Interfaces 2015, vol. 7, pp. 2393-2403.
Zhang "Combination of platelet-rich plasma with degradable bioactive borate glass for segmental bone defect repair" Acta Orthop. Belg. 2011, vol. 77, pp. 110-115.
Hasan et al. "Composition-structure-properties relationship of strontium borate glasses for medical applications" http://onlinelibrary.wiley.com/ DOI: 10.1002/jbm.a.35361, 2014, retrieved on Jan. 16, 2018.
Hidi et al. "The study of the structure and bioactivity of the B2O3 • Na2O • P2O5 system" http://onlinelibrary.wiley.com/ DOI 10.1002/jrs.4330, 2013, retrieved on Jan. 16, 2018.
Huang et al. "Kinetics and mechanisms of the conversion of silicate (45S5), borate, and borosilicate glasses to hydroxyapatite in dilute phosphate solutions" J Mater Sci: Mater Med, 2007, vol. 17, pp. 583-596.
Huang et al. "Conversion of bioactive silicate (45S5) borate, and borosilicate glasses to toxydroxyapatite in dilute phosphate solution" Ceramic Engineering and Science Proceedings, 2007, vol. 27, pp. 131-140.

Yao et al. "Preparation of hollow hydroxyapatite microspheres by the conversion of borate glass at near room temperature" Materials Research Bulletin 2010, vol. 45, pp. 25-28.
Yao et al. "In Vitro Bioactive Characteristics of Borate-Based Glasses with Controllable Degradation Behavior" Journal American Ceramics Society 90 2007, vol. 1, pp. 303-306.
Jung et al. "Potential toxicity of bioactive borate glasses in-vitro and in-vivo" Advances in Bioceramics and Porous Ceramics V 2013, pp. 65-74.
Yang et al. "In vitro study of improved wound-healing effect of bioactive borate-based glass nano-/micro-fibers" Materials Science and Engineering 2015, vol. C55, pp. 105-117.
Peddi et al. "Bioactive borate glass coatings for titanium alloys" J Mater Sci: Mater Med, 2008, vol. 19, pp. 3145-3152.
Lepry et al. "Highly Bioactive Sol-Gel-Derived Borate Glasses" Chemistry Materials., 2015, vol. 27, pp. 4821-4831.
Lepry et al. "Effect of processing parameters on textural and bioactive properties of sol-gel-derived borate glasses" DOI 10.1007/s10853-017-0968-y, retrieved on Jan. 16, 2018.
Liang et al. "Bioactive borate glass scaffold for bone tissue engineering" Journal of Non-Crystalline Solids, 2008, vol. 354, pp. 1690-1696.
Lin et al. "Angiogenic effects of borate glass microfibers in a rodent model" J Biomed Mater Res Part A, 2014, vol. 102A, pp. 4491-4499.
Liu "Bioactive borosilicate glass scaffolds: in vitro degradation and bioactivity behaviors" J Mater Sci: Mater Med, 2009, vol. 20, pp. 1237-1243.
Liu et al. "Conversion of borate-based glass scaffold to hydroxyapatite in a dilute phosphate solution" Biomed. Mater. 2010, vol. 5, pp. 1-6.
Liu et al. "Bioactive borate glass scaffolds: in vitro and in vivo evaluation for use as a drug delivery system in the treatment of bone infection" J Mater Sci: Mater Med 2010, vol. 21, pp. 575-582.
Liu et al. "Porous and strong bioactive glass (13-93) scaffolds prepared by unidirectional freezing of camphene-based suspensions" Acta Biomaterialia 2012, vol. 8, pp. 415-423.
Liu et al. "Conversion of melt-derived microfibrous borate (13-93B3) and silicate (45S5) bioactive glass in a simulated body fluid" J Mater Sci: Mater Med 2013, vol. 24, pp. 583-595.
Liu et al. "In Vitro Degradation and Conversion of Melt-Derived Microfibrous Borate (13-93B3) Bioactive Glass Doped with Metal Ions" Journal American Ceramics Society 2014, vol. 97, pp. 3501-3509.
Lopes et al. "Silicate and borate glasses as composite fillers: a bioactivity and biocompatibility study" J Mater Sci: Mater Med 2011, vol. 22, pp. 1501-1510.
Lu et al. "Enhanced Nonlinear Thin Films of B-Barium Borate by Sol-Gel Synthesis" Chemical Materials 2008, vol. 20, pp. 5296-5300.
Luo et al. In vitro evaluation of cytotoxicity of silver-containing borate bioactive glass http://onlinelibrary.wiley.com/, DOI: 10.1002/jbm.b.31735, 2010, retrieved on Jan. 16, 2018.
MacDonald et al. "Modulation of strontium release from a tertiary borate glass through substitution of alkali for alkali earth oxide" Journal of Non-Crystalline Solids 2016, vol. 443, pp. 184-191.
Manupriya et al. "Compositional dependence of in-vitro bioactivity in sodium calcium borate glasses" Journal of Physics and Chemistry of Solids 2009, vol. 70, pp. 1137-1141.
Margha et al. "Bone bonding ability of some borate bio-glasses and their corresponding glass-ceramic derivatives" Processing and Application of Ceramics 6 2012, vol. 4, pp. 183-192.
Marion et al. "Borate Glass Supports the In Vitro Osteogenic Differentiation of Human Mesenchymal Stem Cells", Mechanics of Advanced Materials and Structures 2005, vol. 3, pp. 239-46.

\* cited by examiner

BORATE-GLASS BIOMATERIALS

FIELD OF THE INVENTION

The invention relates generally to borate-glass biomaterials.

BACKGROUND OF THE INVENTION

Biomaterials are used for the repair, replacement, construction or augmentation of hard and soft tissue in response to diseases, trauma and cosmetic enhancement, as well as drug delivery vehicles.

Bioactive glasses are a type of biomaterial which can be used as bone forming materials for hard tissue applications. Typically, the bioactive glasses are based on silica and comprise a high ratio of calcium to phosphorus to promote formation of apatite crystals, as well as calcium and silica ions to act as crystallization nuclei. However, silica-based glasses tend to have slow and incomplete degradation behaviour. Phosphate based glasses are also attracting attention. Phosphorus-based glasses tend to be more soluble than the silica-based glasses. However, they have limited bioactivity in terms of slow mineralization. Recently, bioactive glasses based on borate have gained in popularity due in part to their faster degradation rate and their potential to be fully biodegradable when compared to traditional silicate glasses. Borate-based glasses are made using melt quench techniques involving oxide precursors melted at high temperatures. This has some drawbacks, such as limiting the ability to incorporate temperature sensitive molecules within the glass due to the high processing temperatures, and not allowing full control of resultant glass microstructure, such as porosity, which is important in biomaterials.

The sol-gel technique is an alternative method for glass production requiring lower processing temperatures and energies than melt quench techniques. Although well established for silica-based glasses, sol-gel methods are still relatively unknown for non-silica based glass networks.

Carta et al (J. Mater. Chem, 2009, 19, p. 150-158) describes a sol-gel method for making borophosphate glasses for biomedical applications comprising a non-siliceous phosphate network incorporating boron. The borophosphate glass systems thus produced are described as $40(P_2O_5)\text{-}x(B_2O_3)\text{-}(60\text{-}x)(Na_2O)$ ($10 \leq x \geq 25$ mol. %) in which the phosphate is the main glass network former. In the sol-gel method of Carta, precursor solutions of phosphorus pentoxide dissolved in anhydrous ethanol, boric acid in methanol solution, and sodium methoxide in methanol are mixed to obtain a sol. Gelation of the sol is said to take 10 days at room temperature. Potential uses of such borophosphates are cited as including degradable temporary implants e.g. for promoting healing or the growth of the surrounding tissue, as well as drug delivery systems.

WO2014/159240 also describes compositions and methods for manufacturing sol-gel derived bioactive borophosphate glasses for medical applications in which the glass is at least 5 wt % CaO, at least 10 wt % $P_2O_5$, at least 10 wt % $Na_2O$, and at least 25 wt % $B_2O_3$, and is substantially silica free. The bioactive glass is said to be useful as hemostatic materials, and for stimulating activity of a gene that promotes wound healing and/or bone regeneration. In one example, precursors of triisopropylborate, ethanol and nitric acid are allowed to react before mixing with calcium methoxyethoxide and sodium ethoxide to form a sol. Ethanol and nitric acid are then added to the sol before gelation which takes 24 hours at 60° C. In another example, triethylphosphate and nitric acid are mixed before adding triisopropylborate, calcium methoxyethoxide and sodium ethoxide to form a sol. Ethanol and nitric acid are then added until gelation occurs and this step is maintained at 60° C. for 24 hours to complete the reaction. The compositions thus produced are assumed to have either a phosphate network or a shared phosphate-boron network. It is desired to provide alternative or improved bioactive glass biomaterials and/or methods of manufacture.

SUMMARY OF THE INVENTION

The aspects and embodiments of the present disclosure provide a novel borate-based glass biomaterial, and uses of the same. The aspects and embodiments of the present disclosure also provide a novel sol-gel based method of making a bioactive glass.

The biomaterial disclosed herein has a high specific surface area, is amorphous, and fully soluble, and has been shown by the inventors to form hydroxyapatite rapidly in the absence of cells when in contact with simulated body fluid, a representative and accepted in vitro model for in vivo mineralisation behaviour. Surprisingly, the inventors have found that in certain embodiments, mineralisation was initiated within 3 hours of contact with simulated body fluid and full conversion to hydroxyapatite occurred between about 1 to about 3 days, as measured using XRD. However, surface mineralisation was observed within 30 minutes of contact with simulated body fluid. In the borate-based glass biomaterial of the present disclosure, borate is the sole and main network former and is therefore distinct from glasses containing boron where the borate is a modifier and not the major glass network former or shares this network forming role, such as in borophosphate, aluminoborate and aluminoborosilicate glasses of the prior art.

From one aspect, there is provided a borate glass biomaterial comprising sol-gel derived bioactive glass wherein the bioactive glass has borate as the sole network forming component and which generates hydroxyapatite when contacted with simulated body fluid. From another aspect there is provided a four component glass biomaterial including an oxide of sodium, an oxide of calcium, and oxide of phosphorus and an oxide of boron. The biomaterial comprises: $aNa_2O \cdot bCaO \cdot cP_2O_5 \cdot dB_2O_3$, wherein a is from about 1-40 wt %, b is from about 10-40 wt %, c is from about 1-40 wt %, and d is from about 35-80 wt %; and wherein the biomaterial has a surface area per mass of more than about 5 m²/g. In certain embodiments, the biomaterial is a sol-gel derived amorphous glass.

From another aspect there is provided an amorphous biomaterial comprising: $aNa_2O \cdot bCaO \cdot cP_2O_5 \cdot dB_2O_3$, wherein a is from about 1-40 wt %, b is from about 10-40 wt %, c is from about 1-40 wt %, and d is from about 35-80 wt %; and wherein the biomaterial has a surface area per mass of more than about 5 m²/g. In certain embodiments, d is more than about 40 wt %. In certain embodiments, c is less than about 10 wt %. From a further aspect, there is provided a sol-gel derived amorphous glass composition comprising: $aNa_2O \cdot bCaO \cdot cP_2O_5 \cdot dB_2O_3$, wherein a is from about 1-40 wt %, b is from about 10-40 wt %, c is from about 1-40 wt %, and d is from about 35-80 wt %. In certain embodiments, d is more than about 40 wt %. In certain embodiments, c is less than about 10 wt %.

From a yet further aspect, there is provided a sol-gel derived borate-glass composition comprising: $aNa_2O \cdot bCaO \cdot cP_2O_5 \cdot dB_2O_3$, wherein a is from about 1-40 wt %, b is from about 10-40 wt %, c is less than about 10 wt %, and d is from about 35-80 wt %, and wherein the borate is the sole network former. In certain embodiments, d is more than about 40 wt %. In certain embodiments, the biomaterial has a surface area per mass of more than about 5 m$^2$/g.

In certain embodiments of any of the foregoing or the following, a is from about 15-30 wt %, b is from about 15-30 wt %, c is from about 3-7 wt %, and d is from about 35-65 wt %, or a is about 16-27 wt %, b is about 16-27 wt %, c is about 4-7 wt % and d is about 39-63 wt %. In certain embodiments of any of the foregoing or the following, c is less than about 10 wt %. In certain embodiments of any of the foregoing or the following, d is more than about 40 wt %.

In certain embodiments of any of the foregoing or following, the biomaterial has a higher borate content than the content of any of the other components individually. For example, the borate content is more than the calcium content, or the phosphorus content or the sodium content. In certain embodiments of any of the foregoing or following, the presently disclosed biomaterial has borate as its sole network forming component. This is distinct from glasses containing boron where borate is not the sole network former such as in borophosphate, aluminoborate and aluminoborosilicate glasses.

In certain embodiments of any of the foregoing or following, Na$_2$O can be replaced by any other suitable basic oxide such as an alkali metal e.g. K$_2$O, or RB$_2$O. From yet another aspect, there is provided a three component glass biomaterial comprising an oxide of calcium, an oxide of phosphorus and an oxide of borate. The biomaterial does not contain any sodium other than possibly trace amounts. The biomaterial comprises: xCaO. yP$_2$O$_5$. zB$_2$O$_3$, wherein x is from about 5-50 wt %, y is from about 5-50 wt %, and z is from about 35-75 wt %; and wherein the biomaterial has a surface area per mass of more than about 5 m$^2$/g. In one embodiment, x is 10-50 wt %, y is 5-35 wt % and z is 38-80 wt %. In certain embodiments, the borate is sole network forming component.

From a further aspect, there is provided a biomaterial comprising: xCaO. yP$_2$O$_5$. zB$_2$O$_3$, wherein x is from about 5-50 wt %, y is from about 5-50 wt %, and z is from about 35-75 wt %. In one embodiment, x is 10-50 wt %, y is 5-35 wt % and z is 38-80 wt %. In certain embodiments, y is less than about 10 wt %. In certain embodiments, the borate is sole network forming component.

From yet another aspect, there is provided a three component glass biomaterial comprising an oxide of sodium, an oxide of calcium and an oxide of boron. The biomaterial does not contain any phosphorus other than possibly trace amounts. The biomaterial comprises: lNa$_2$O. mCaO. nB$_2$O$_3$, wherein l is from about 5-50 wt %, m is from about 1-50 wt %, and n is from about 40-80 wt %; and wherein the biomaterial has a surface area per mass of more than about 5 m$^2$/g. In certain embodiments of any of the foregoing or following, the biomaterial has a surface area per mass of more than about 10 m$^2$/g, more than about 20 m$^2$/g, more than about 30 m$^2$/g, more than about 40 m$^2$/g, or more than about 50 m$^2$/g.

In certain embodiments of any of the foregoing or following, the biomaterial has a surface area per mass of about 5-300 m$^2$/g, 10-300 m$^2$/g, 20-300 m$^2$/g, 30-300 m$^2$/g, 40-300 m$^2$/g, 50-300 m$^2$/g, 60-300 m$^2$/g, 70-300 m$^2$/g, 80-300 m$^2$/g, 90-300 m$^2$/g, 100-300 m$^2$/g, 110-300 m$^2$/g, 120-300 m$^2$/g, 130-300 m$^2$/g, 140-300 m$^2$/g, 150-300 m$^2$/g, 200-300 m$^2$/g, 250-300 m$^2$/g, 5-250 m$^2$/g, 5-200 m$^2$/g, 5-150 m$^2$/g or 5-100 m$^2$/g. All surface area per mass measurements are as measured using the isotherm with the Brunauer-Emmett-Teller (BET) method (S. Brunauer, P. H. Emmett, E. Teller, Adsorption of gases in multimolecular layers. *Journal of the American Chemical Society* 60, 309-319 (1938)).

In certain embodiments of any of the foregoing or following, the biomaterial has a pore volume per mass of biomaterial which is more than about 0.001 cm$^3$/g, more than about 0.01 cm$^3$/g, more than about 0.02 cm$^3$/g, more than about 0.03 cm$^3$/g, more than about 0.04 cm$^3$/g, more than about 0.05 cm$^3$/g, more than about 0.06 cm$^3$/g, more than about 0.07 cm$^3$/g, more than about 0.08 cm$^3$/g, more than about 0.09 cm$^3$/g, more than about 0.1 cm$^3$/g, more than about 0.2 cm$^3$/g, more than about 0.3 cm$^3$/g, or more than about 0.4 cm$^3$/g.

In certain embodiments of any of the foregoing or following, the biomaterial has a pore volume per mass of biomaterial which ranges from about 0.1-3.0 cm$^3$/g, 0.2-3.0 cm$^3$/g, 0.3-3.0 cm$^3$/g, 0.4-3.0 cm$^3$/g, 0.5-3.0 cm$^3$/g, 0.6-3.0 cm$^3$/g, 0.7-3.0 cm$^3$/g, 0.8-3.0 cm$^3$/g, 0.9-3.0 cm$^3$/g, 1.0-3.0 cm$^3$/g, 0.1-2.5 cm$^3$/g, 0.42-1.18 cm$^3$/g or 0.1-2.0 cm$^3$/g.

In certain embodiments of any of the foregoing or following, the biomaterial is bioactive. In some embodiments, the biomaterial can induce bone formation. Bone formation may comprise apatite formation such as hydroxyapatite formation in the absence or presence of cells.

In certain embodiments of any of the foregoing or following, the biomaterial is biodegradable. Advantageously, the biomaterial is substantially free of silica other than possibly trace amounts. As the biomaterial is not silica-based, advantageously in certain embodiments it is fully biodegradable. In certain embodiments of any of the foregoing or following, the biomaterial/composition is substantially free of alumina.

In certain embodiments of any of the foregoing or following, the biomaterial is amorphous. In certain embodiments of any of the foregoing or following, the biomaterial is a glass. In certain embodiments, the biomaterial is crystalline or semi-crystalline.

In certain embodiments of any of the foregoing or following, the biomaterial is in particulate form. The particle size may range from 0.2-1 μm, 5-2000 μm, 5-100 μm, or 25-75 μm, or any other size which is biologically relevant.

In certain embodiments of any of the foregoing or following, the biomaterial is in a fibrillar form, a particulate form, a hollow spherical form, a bead form, a solid spherical form, conical form, wedge shaped, cylindrical, thin film, foam form, sponge form or a monolithic form. Other shapes are also possible, as well as a range of sizes. Biomaterials in the form of thin films are useful as coatings.

In certain embodiments of any of the foregoing or following, the biomaterial further comprises trace elements of about 0.05 to about 10 wt. % or about 0.05 to about 30 wt. % of one or more of Ti, Li, Si, Au, Ag, Cu, Co, F, Fe, Mn, Mo, Mg, Ni, Rb, Sr, K, Ga, and Zn. In certain embodiments of any of the foregoing or following, the biomaterial further comprises a carrier. The carrier may be a synthetic polymer selected from the group consisting of vinyl polymers, polyoxyethylene-polyoxypropylene copolymers, poly(ethylene oxide), acrylamide polymers and derivatives or salts thereof. The vinyl polymer may be selected from the group of polyacrylic acid, polymethacrylic acid, polyvinyl pyrrolidone or polyvinyl alcohol. The carrier may be a carboxy vinyl polymer or a carbomer obtained by polymerisation of acrylic acid.

In certain embodiments, the carrier comprises a protein-based polymer selected from at least one of sodium hyaluronate, hyaluronan, gelatin and collagen.

In certain embodiments, the carrier comprises a polysaccharide selected from at least one of starch, chitosan, chitin, agar, alginates, xanthan, carrageenan, guar gum, gellan gum, pectin, and locust bean gum.

In certain embodiments, the carrier is a liquid such as blood, water, saline or simulated body fluids. The biomaterial may be a slurry, an emulsion, a gel, a putty or a paste. The carrier may be a paste or a slurry such as mouthwash or toothpaste.

In certain embodiments, the carrier is a hydrogel.

The carrier may comprise a bone or defect filler material such as polymethylmethacrylate or calcium phosphate based bone cements.

In certain embodiments of any of the foregoing or following, the biomaterial may comprise one or more bioactive agents selected from cells, genes, drug molecules, therapeutic agents, particles, osteogenic agents, osteoconductive agents, osteoinductive agents, anti-inflammatory agents, antibiotics, anticoagulants, growth factors, and the like. The biomaterial may be used as a delivery vehicle for these bioactive agents.

Examples of cells include those involved in hard and soft tissue generation, regeneration, repair and maintenance, for example embryonic or mesenchymal stem cells, bone marrow stem cell, osteoblasts, preosteoblasts, fibroblasts, nerve cells, muscle cells, myoblasts, fibroblasts, populations of cells such as from a bone marrow aspirate, chondrocytes, and the like. Combinations of cell types can also be included. Therapeutic agents can include hormones, bone morphogenic proteins, antimicrobials, anti-rejection agents and the like. Examples of drugs include any molecules for disease, condition or symptom treatment or control, anti-inflammatory, growth factors, peptides, antibodies, vesicle for release of ions, release of gas, release of nutrients, enzymes, as well as nano carriers. The particles can be fibroin-derived polypeptides, preferably polypeptides which have been chymotryptically isolated and extracted from silk fibroin such as a soluble fraction Cs, a precipitated fraction Cp, or a combination of the Cs and Cp fractions (as described in PCT/CA2012/000192, the contents of which are herein incorporated by reference).

In certain embodiments of any of the foregoing or following, the biomaterial is coated on an implant surface, such as a bone implant. The biomaterial can also be coated onto hard tissue such as bone or teeth. In certain embodiments, the biomaterial may be used for bone mass increase for tooth implants, endosseus ridge bone enhancement for denture fixation, as well as maxillofacial and orthopaedic uses. The biomaterial may also be useful as a haemostatic material, such as a hemostatic sponge, by virtue of its high surface area. The biomaterial may also be used as a cosmetic for skin for exfoliation and generally improving skin properties. The biomaterial may also be used an antibacterial agent.

From a further aspect, there is provided a method for making the biomaterial as described herein, the method comprising: combining precursor solutions containing boron ions, phosphate ions, sodium ions and calcium ions to form a solution; gelling the solution to form a gel; drying the gel; and calcining the dried gel.

From a yet further aspect, there is provided a method for making the biomaterial as described herein, the method comprising: combining precursor solutions containing boron ions, phosphate ions, and calcium ions to form a solution; gelling the solution to form a gel; drying the gel; and calcining the dried gel.

In certain embodiments of any of the foregoing or following, the gelling step includes allowing the gels to age for example at room temperature or at temperatures higher than room temperature for about 2-15 days or until gel formation has stabilized or completed. In certain embodiments of any of the foregoing or following, an ageing step is not necessary as gelation may stabilize rapidly.

In certain embodiments of the foregoing or following, gelling the solution comprises maintaining the solution at a temperature between about room temperature and about 60° C., preferably at about 37° C. There may also be included a step of ageing the gel comprising allowing it to rest at room temperature or at elevated temperatures.

In certain embodiments of any of the foregoing or following, the precursor solutions are combined at a temperature of between about room temperature and about 38° C., preferably at about 37° C., about 36° C., about 35° C., about 34° C., about 33° C., about 32° C., about 31° C., about 30° C., about 29° C., about 28° C., about 27° C., about 26° C., about 25° C., about 24° C., about 23° C., about 22° C., or about 21° C.

In certain embodiments of any of the foregoing or following, the gelling step takes place at a temperature of between about room temperature and about 38° C., preferably at about 37° C., about 36° C., about 35° C., about 34° C., about 33° C., about 32° C., about 31° C., about 30° C., about 29° C., about 28° C., about 27° C., about 26° C., about 25° C., about 24° C., about 23° C., about 22° C., or about 21° C.

In certain embodiments of any of the foregoing or following, the gelling step takes place in less than about 12 hours, less than about 10 hours, less than about 8 hours, less than about 6 hours, less than about 4 hours, less than about 2 hours, less than about 1 hour, less than about 30 minutes, or between about 5 minutes and about 30 minutes. Gelation of the solution is considered to have occurred if no flow is observed when a vial containing the solution is held upside down at room temperature and pressure and no flow is observed.

In certain embodiments of any of the foregoing or following, an ageing step is not necessary as gelation may stabilize rapidly.

In certain embodiments of any of the foregoing or following, the pH of the solution after adding the final precursor is, or is adjusted to, more than about 10, more than about 10.5, more than about 11, more than about 11.5, more than about 12, or more than about 12.5. In certain embodiments of any of the foregoing or following, the pH of the solution after adding the final precursor is between about 10.5 and about 14.0, or about 11 and about 13.5.

In certain embodiments of the foregoing or following, the precursor solution containing boron ions is selected from one or more of trimethyl borate $B(OCH_3)_3$, triethyl borate $B(C_2H_5O)_3$, tributyl borate $B(CH_3(CH_2)_3O)_3$, Tri-tert-butyl borate $B_3(CH_3)_3CO$ and boric acid $H_3BO_3$. Preferably, the boron ion precursor solution is boric acid which may be dissolved in ethanol.

In certain embodiments of the foregoing or following, the precursor solution containing calcium ions is selected from one or more of calcium methoxyethoxide, Calcium nitrate tetrahydrate ($Ca(NO_3)_2 4H_2O$), Calcium Chloride ($CaCl_2$), Calcium Ethoxide ($Ca(C_2H_5O)_2$), and Calcium methoxide ($C_2H_6CaO_2$).

In certain embodiments of the foregoing or following, the precursor solution containing phosphate ions is selected from one or more of triethyl phosphate, Trimethyl phosphate (($CH_3)_3PO_4$), Tributyl phosphate (($CH_3CH_2CH_2$ $CH_2O)_3PO$), Dibutyl phosphate ($(CH_3CH_2CH_2CH_2O)_2P(O)OH$), n-Butyl phosphate, mixture of monobutyl and dibutyl ($C_8H_{19}O_4P/C_4H_{11}O_4P$).

In certain embodiments of the foregoing or following, the precursor solution containing sodium ions is selected from one or more of sodium methoxide ($NaCH_3O$) in methanol (25% or 30%), sodium ethoxide and sodium hydroxide (NaOH).

In certain embodiments of the foregoing or following, the precursor solutions comprise boric acid, triethyl phosphate, calcium methoxyethoxide, and sodium methoxide.

In certain embodiments of the foregoing or following, the precursor solutions comprise boric acid, triethyl phosphate and calcium methoxyethoxide (20% in methoxyethanol).

Advantageously, the boric acid is dissolved in ethanol. In certain embodiments, the boric acid is dissolved in ethanol at a temperature at or higher than room temperature, at temperatures between about room temperature and 38° C., at about 37° C., about 36° C., about 35° C., about 34° C., about 33° C., about 32° C., about 31° C., about 30° C., about 29° C., about 28° C., about 27° C., about 26° C., about 25° C., about 24° C., about 23° C., about 22° C., or about 21° C. Advantageously, boric acid has a higher solubility in ethanol at higher temperatures which means that when the mixing step is carried out at 37° C., for example, less ethanol is required to dissolve the boric acid.

In certain embodiments of any of the foregoing or following, the precursor solutions are added sequentially. In certain embodiments of the foregoing or following, the precursor solutions having a basic pH are added after those with a low pH.

In certain embodiments, the mixing of the precursor solutions is performed in a single pot. Advantageously, this means that this process can be easily scaled-up.

In certain embodiments of any of the foregoing or following, a pH adjusting agent can be used to adjust the pH of the solution after mixing the precursors. The pH adjusting agents can be selected from NaOH, KOH, LiOH, ammonia, calcium hydroxide ($Ca(OH)_2$), and strontium hydroxide ($Sr(OH)_2$). The method may further comprise grinding the calcined dried gel to form particles of any desired size.

In certain embodiments of the foregoing or following, drying the gel comprises heating the gel and/or allowing loss of humidity to form a dry gel.

In certain embodiments of the foregoing or following, calcining the dry gel comprises heating the dry gel to between about 400-600° C. This may eliminate all organic contamination. Alternatively, calcining the dry gel can comprise heating to between about 100 to about 400° C., or from about 120 to about 400° C., or from about 150 to about 400° C., or from about 200 to about 400° C.

In certain embodiments of the foregoing or following, heating comprises using a 3° C./min heating rate, followed by a 2 hour dwell, and then furnace cooling.

In certain embodiments of the foregoing or following, the method comprises combining the gel with a polymer or binder and drying under controlled conditions such as those using critical point drying. This may provide a biomaterial with a monolithic structure and avoid collapse.

In certain embodiments of the foregoing or following, the method comprises a processing step after gelation to make fibres (e.g. by electrospinning, solution blow-spinning etc), thin films, or hollow particles.

From another aspect, there is provided use of the biomaterial as herein described for bone regeneration, for supporting direct axon growth, wound healing, filling or repairing hard or soft tissue defects or as a coating on an implant such as a bone implant or hard tissue surface. Examples of soft tissue include vascularization, wound healing, cartilage, skin, muscle, tendon, ligament, cornea, iris, periodontal tissue, bladder, cardiac, lung, nerve, gastrointestinal, urinary tract and laryngeal tissue repair. In certain embodiments, the biomaterial can be incorporated into a polymer matrix, degradable or otherwise, to create bioactive composite systems. The composite can be in a monolithic form, a fibrous form, or a porous sponge scaffold form. The volume fraction of the biomaterial in the composition system can range from about 0.0001 to about 0.7. There is also provided use of the biomaterial described herein for drug or other bioactive agent delivery, as well as wound healing, antimicrobial use. Also provided is use of the biomaterial described herein as a hemostatic material, such as a sponge.

There is also provided use of the biomaterial as described herein as a cosmetic for skin for exfoliation, for improving skin properties, for reducing skin redness, for reducing the appearance of wrinkles, for reducing the appearance of ageing, or for skin oxidative properties. The biomaterial may be included within a cream or a paste for application to skin. Hyaluronan or any other cosmetic cream or serum can be used as a carrier for the biomaterial. There is also provided use of the biomaterials as described herein for reducing dentine sensitivity.

Advantageously, the high surface area of certain embodiments of the present biomaterials results in faster ionic release and degradation which may improve bioactivity by affecting cellular response and promoting quicker tissue regeneration.

Advantageously, embodiments of the present method allow for greater flexibility in composition because of the low processing temperature compared to melt methods, and hybrid materials are easily obtained. In embodiments of the present method, the glassy network is created by hydrolysis and condensation reactions of liquid precursors which are typically metal alkoxides. Furthermore, embodiments of the present method allow for tailoring of the surface area, porosity and hence bioactivity of the resultant biomaterials for a targeted cellular response.

Advantageously, embodiments of the present method do not require the addition of water. In contrast, in traditional sol-gel methods, water is added to induce hydrolysis of the precursor materials and to allow for condensation creating the initial sol. In certain embodiments of the present method, boric acid is added to ethanol which creates triethyl borate (TEB) and water as seen in equation 1.

$$H_3BO_3 + 3(C_2H_6OH) \rightarrow B(C_2H_5O)_3 + 3(H_2O) \qquad \text{(eqn. 1)}$$

It is believed that excess water formed by this reaction hydrolyzes the newly formed TEB creating terminal OH⁻ groups which undergo condensation forming the initial sol and eventually the gel network. These processes can also happen at the same time. The Ca and TEP sources incorporate themselves into the network during processing.

The inventors found that with certain embodiments of the disclosed method and biomaterial, a rapid gelation was observed. In certain embodiments, gelation was achieved within 30 minutes of adding the final precursor. Shorter biomaterial processing times are economically desirable. Advantageously, the sol-gel method presently described is a simple method which can be scaled up. As demonstrated in the Examples, sol-gel derived, borate glasses suitable for biomedical applications such as bone tissue engineering applications have been created. The ability to rapidly form hydroxyapatite in vitro using simulated body fluids was demonstrated by certain embodiments of the present biomaterials as demonstrated in the Examples, and mesenchymal stem cell (MSC) compatibility was observed demonstrating that these biomaterials can be used in vivo.

Definitions:

The term "Surface area by mass" as used herein means: The total external surface area ($m^2$) related to the mass (g) of the material. Also referred to as "specific surface area" and expressed as ($m^2/g$).

The term "Pore volume" as used herein means: The total volume of the pores ($cm^3$) within a set amount of material (g). Often expressed as $cm^3/g$. The term "biomaterial" as used herein means: a material that is biocompatible with a human or animal body when in contact with the body such as by implantation, injection or any other contact. It can be in liquid, gel or solid form.

The term "borate" as used herein means an oxide of Boron including but not limited to $B_2O_3$.

The term "substantially silica free" means: there is no silica content other than trace amounts which may be present.

BRIEF DESCRIPTION OF THE DRAWINGS

Further aspects and advantages of the present invention will become better understood with reference to the description in association with the following in which.

DETAILED DESCRIPTION OF THE INVENTION

Figure 1:
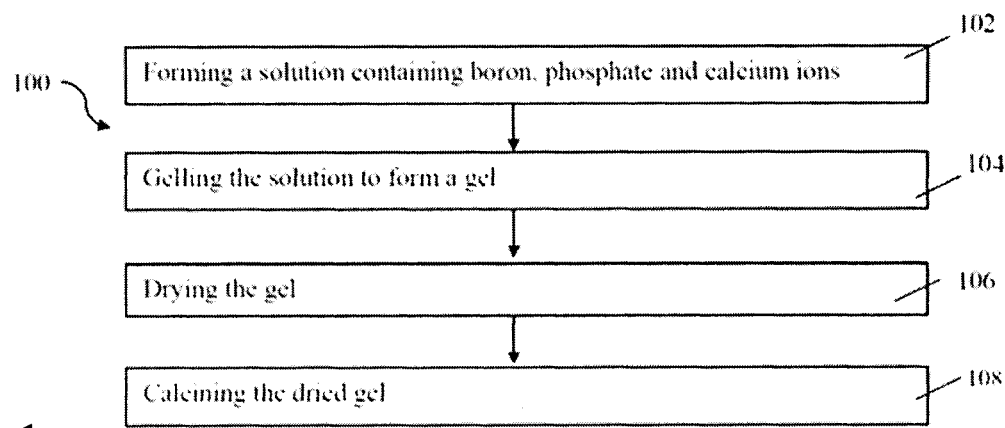
FIG. 1 is a schematic of an embodiment of a method for making a biomaterial according to the present disclosure.

This invention is not limited in its application to the details of construction and the arrangement of components set forth in the following description or illustrated in the drawings. The invention is capable of other embodiments and of being practiced or of being carried out in various ways. Also, the phraseology and terminology used herein is for the purpose of description and should not be regarded as limiting. The use of "including", "comprising", or "having", "containing", "involving" and variations thereof herein, is meant to encompass the items listed thereafter as well as, optionally, additional items. In the following description, the same numerical references refer to similar elements. In the drawings, like reference characters designate like or similar parts.

One aspect of the present disclosure is directed to biomaterials which comprise a borate-glass. In one embodiment, the biomaterial comprises: $aNa_2O \cdot bCaO \cdot cP_2O_5 \cdot dB_2O_3$, wherein a is from about 1-40 wt %, b is from about 10-40 wt %, c is from about 1-40 wt %, and d is from about 35-80 wt %; and wherein the biomaterial has a surface area per mass of more than about 5 $m^2/g$.

In another embodiment, the biomaterial comprises: $xCaO \cdot yP_2O_5 \cdot zB_2O_3$, wherein x is from about 5-50 wt %, y is from about 5-50 wt %, and z is from about 35-75 wt %; and wherein the biomaterial has a surface area per mass of more than about 5 $m^2/g$.

In another embodiment, the biomaterial comprises: $lNa_2O \cdot mCaO \cdot nB_2O_3$, wherein l is from about 5-50 wt %, m is from about 1-50 wt %, and n is from about 40-80 wt %; and wherein the biomaterial has a surface area per mass of more than about 5 $m^2/g$. In certain embodiments of any of the foregoing or following, the biomaterial has a surface area per mass of more than about 10 $m^2/g$, more than about 20 $m^2/g$, more than about 30 $m^2/g$, more than about 40 $m^2/g$, or more than about 50 $m^2/g$.

The surface area per mass of the biomaterial is about 5-300 $m^2/g$, 10-300 $m^2/g$, 20-300 $m^2/g$, 30-300 $m^2/g$, 40-300 m$^2$/g, 50-300 m$^2$/g, 60-300 m$^2$/g, 70-300 m$^2$/g, 80-300 m$^2$/g, 90-300 m$^2$/g, 100-300 m$^2$/g, 110-300 m$^2$/g, 120-300 m$^2$/g, 130-300 m$^2$/g, 140-300 m$^2$/g, 150-300 m$^2$/g, 200-300 m$^2$/g, 250-300 m$^2$/g, 5-250 m$^2$/g, 5-200 m$^2$/g, 5-150 m$^2$/g or 5-100 m$^2$/g. The pore volume per mass of biomaterial is about 0.1-3.0 cm$^3$/g, 0.2-3.0 cm$^3$/g, 0.3-3.0 cm$^3$/g, 0.4-3.0 cm$^3$/g, 0.5-3.0 cm$^3$/g, 0.6-3.0 cm$^3$/g, 0.7-3.0 cm$^3$/g, 0.8-3.0 cm$^3$/g, 0.9-3.0 cm$^3$/g, 1.0-3.0 cm$^3$/g, 0.1-2.5 cm$^3$/g, 0.42-1.18 cm$^3$/g or 0.1-2.0 cm$^3$/g.

In one embodiment the biomaterial is amorphous and is in particulate form with a particle size of about 5-2000 μm. The biomaterial may be used for bone regeneration or augmentation and may be placed in a bone defect or at a site requiring bone augmentation.

The biomaterial may be made into a slurry using the patient's own blood or bone before packing into the defect. The biomaterial may also be injected. From another aspect, there is provided a method 100 of making the biomaterials described herein (FIG. 1).

In one embodiment of the method 100, the method comprises an adapted sol-gel method. Briefly, the method comprises forming a solution to be gelled 102, gelling the solution to form a gel 104, drying the gel to form a dry gel 106, calcining the dry gel to remove organic matter 108, and optionally grinding the calcined dry gel, and/or sizing the calcined dry gel to obtain particles within a certain size and/or shape range.

In one embodiment, forming the solution comprises mixing together precursors. The precursors comprise boric acid, triethyl phosphate, calcium methoxyethoxide (20% in methoxyethanol), and sodium methoxide. Gelling the solution comprises casting the solution into sealed vials and placing in an oven at 37° C. The gelled solution may also be left to age at room temperature or elevated temperatures for example for about 2-15 days. In one embodiment, drying the gels comprises removing from the oven and placing in crystallization dishes to dry at room temperature for a day then in an oven at 120° C. for 2 days. In some embodiments, the drying step causes the gel to dry to a particulate form. Calcining the dry gel comprises heating (400-600° C.) in air using a 3° C./min heating rate, 2 hour dwell, and furnace cooling. In certain embodiments, the method comprises grinding the calcined dry gel and sieving to a desired size range such as 25-75 μm.

Other starting solutions (precursors) can include:
For Boron: Trimethyl borate B(OCH$_3$)$_3$, triethyl borate B(C$_2$H$_5$O)$_3$, tributyl borate B(CH$_3$(CH$_2$)$_3$O)$_3$, Tri-tert-butyl borate (B$_3$(CH$_3$)$_3$CO)
For Calcium: Calcium nitrate tetrahydrate (Ca(NO$_3$)$_2$·4H$_2$O), Calcium Chloride (CaCl$_2$), Calcium Ethoxide (Ca(C$_2$H$_5$O)$_2$), Calcium methoxide (C$_2$H$_6$CaO$_2$)
For Sodium: Sodium methoxide (NaCH$_3$O) in methanol (different %), Sodium hydroxide (NaOH)
For Phosphate: Trimethyl phosphate ((CH$_3$)$_3$PO$_4$), Tributyl phosphate ((CH$_3$CH$_2$CH$_2$CH$_2$O)$_3$PO), Dibutyl phosphate ((CH$_3$CH$_2$CH$_2$CH$_2$O)$_2$P(O)OH), n-Butyl phosphate, mixture of monobutyl and dibutyl (C$_8$H$_{19}$O$_4$P/C$_4$H$_{11}$O$_4$P)

A second embodiment of the method differs from the first embodiment in that sodium ions are not included. In this case, the method comprises mixing boric acid, triethyl phosphate and calcium methoxyethoxide (20% in methoxyethanol) and following the same procedure as described for the first embodiment.

A third embodiment of the method differs from the first embodiment in that phosphorus ions are not included. In this case, the method comprises mixing boric acid, sodium methoxide and calcium methoxyethoxide (20% in methoxyethanol) and following the same procedure as described for the first embodiment.

Identification of equivalent compositions and methods are well within the skill of the ordinary practitioner and would require no more than routine experimentation, in light of the teachings of the present disclosure. Practice of the disclosure will be still more fully understood from the following examples, which are presented herein for illustration only and should not be construed as limiting the disclosure in any way.

EXAMPLES

Example 1

Method of Making Borate-Glass Biomaterials

Borate-glass biomaterials, according to certain embodiments of the present disclosure, were made using a sol-gel process. All sol-gel processing took place within a nitrogen purged glove box. Four component borate glass compositions based on boron, Ca, Na and P were made by incrementally increasing or decreasing the amount of boron while maintaining the ratio of the Ca, Na, and P (Table 1). Boric Acid (>99.5%) was first added to anhydrous ethanol in a Teflon beaker which was covered with a watch glass, stirred magnetically, and heated to about 35-50° C., preferably 40° C.±3° C., to aid dissolution. Advantageously, unlike most known sol gel methods, a mild heating of about 35-50° C. suffices. After the solution became clear, triethyl phosphate (>99.8%), calcium methoxyethoxide (20% in methoxyethanol), and sodium methoxide (25 wt. % in methanol) were added drop wise in 30 minute intervals. After the final addition the solution was mixed for another 30 minutes or until the viscosity became too great for stirring.

The sol was then cast into polypropylene vials (4 mL capacity. O. D.×Height: 13×57 mm), sealed, and stored in an oven at 37° C. for further gelation and ageing. In some instances, gelation, or partial gelation, occurred within the mixing vessel before casting. After 10 days the gels were removed as monolithic gels and placed in crystallization dishes and dried in air at room temperature for one day, then in an oven at 120° C. for 2 days. During the first part of the drying, all gel monoliths collapsed into particles. The collapsing of the monolithic gel is often observed with non-silicate sol-gel systems and is extremely difficult to avoid even with controlled methods. In order to prevent this collapse and to create a monolith structure, the gel can be combined with a polymer or binder and dried under controlled conditions such as those using critical point drying.

Monolithic gels also formed in larger containers (60 mL capacity: O.D.×Height: 53×47 mm) demonstrating the ability to scale-up this process. The particles were then calcined in air to various temperatures (400° C., 450° C., 500° C., 550° C. and 600° C.) using a 3° C./min heating rate, 2 hour dwell time, and then furnace cooled. Lower calcination temperatures (100° C. to 400° C.) are also possible. Following calcination, the particles were ground and sieved to isolate a particle size fraction of 25-75 μm and stored in a desiccator until analysis. For traditional, melt derived bioactive glasses, sodium is often added to help reduce the firing temperature of the glass melt but for sol-gel derived glasses this is not necessary due to the low processing conditions. However to directly compare the biomaterial of the present disclosure to melt-derived biomaterials of similar compositions (Example 2), sodium was added.

TABLE 1

Biomaterial compositions made in Example 1 according to embodiments of the present disclosure.

| | wt. % (mol %) | | | |
|---|---|---|---|---|
| ID | $B_2O_3$ | CaO | $Na_2O$ | $P_2O_5$ |
| B36 | 38.6 (36.2) | 27.4 (31.90) | 27.4 (28.9) | 6.6 (3.0) |
| B41 | 43.6 (41.1) | 25.2 (29.4) | 25.2 (26.6) | 6.1 (2.8) |
| B46 | 48.6 (46.1) | 22.9 (26.9) | 22.9 (24.4) | 5.6 (2.6) |
| B51 | 53.6 (51.1) | 20.7 (24.4) | 20.7 (22.1) | 5.1 (2.4) |
| B56 | 58.6 (56.1) | 18.4 (21.9) | 18.4 (19.8) | 4.6 (2.2) |
| B61 | 63.6 (61.3) | 16.2 (19.3) | 16.2 (17.5) | 4.1 (1.9) |

Each biomaterial formulation of Table 1 successfully underwent gelation even at low boron concentrations as confirmed qualitatively by holding the storage vials upside down and noting no flow at room temperature, although for the lowest boron concentration, B36, gelation did not occur until the second day.

The pH of the solution was measured immediately after addition of the sodium precursor and before casting, and were as follows: B36, pH 13.3; B41, pH 13.1; B46, pH 13.1; B51, pH 12.9; B56, pH 12.7 and B61, pH 11.2. During addition of the precursors, the pH was found to increase rapidly from about 3 to about 11 after addition of the calcium precursor.

Instead of boric acid being added to ethanol, traditional sol gel precursors of triethyl borate, trimethyl borate and tributyl borate were individually tried within the method of Example 1. However, with these precursors, there was no gel formation suggesting no network formation although they did form a glass.

Example 2

Comparative Example

To compare the effect of processing methods, a borate-glass biomaterial with a substantially equivalent composition (Table 2) to that of B46 of Example 1 was created using a melt quench technique. Boric Acid, monosodium phosphate, sodium carbonate, and calcium carbonate were thoroughly dry mixed and placed in a Pt crucible then heated at 1100° C. for 2 hours with intermediate stirring to insure homogeneity. The melt was then rapidly quenched between two steel plates and the resultant glass ground to 25-75 μm particles. The comparative biomaterial thus obtained, and the method used to obtain it, does not form part of the present disclosure and is included here for comparison purposes only.

TABLE 2

Comparative example of melt-derived composition.

| | wt. % (mol %) | | | |
|---|---|---|---|---|
| ID | $B_2O_3$ | CaO | $Na_2O$ | $P_2O_5$ |
| Comparative Example 45B5 | 48.6 (46.1) | 22.9 (26.9) | 22.9 (24.4) | 5.6 (2.6) |

Example 3

Effect of Calcination Temperature on Crystallinity of the Glasses of Example 1

The effect of calcination temperature (400-600° C., and as-made (AM)) on structure for the sol-gel glasses of Example 1 was investigated using X-ray diffractometry (XRD). The sol-gel derived glass powders of Example 1 were analyzed with a Bruker D8 Discover™ X-ray diffractometer equipped with a CuKα (λ=0.15406 nm) target set to a power level of 40 mV and 40 mA. Using an area detector, three frames of 25° were collected from 15-75 2 theta) (°) and merged in post processing. Phase identification was carried out using X'Pert Highscore Plus™.

Figure 2:
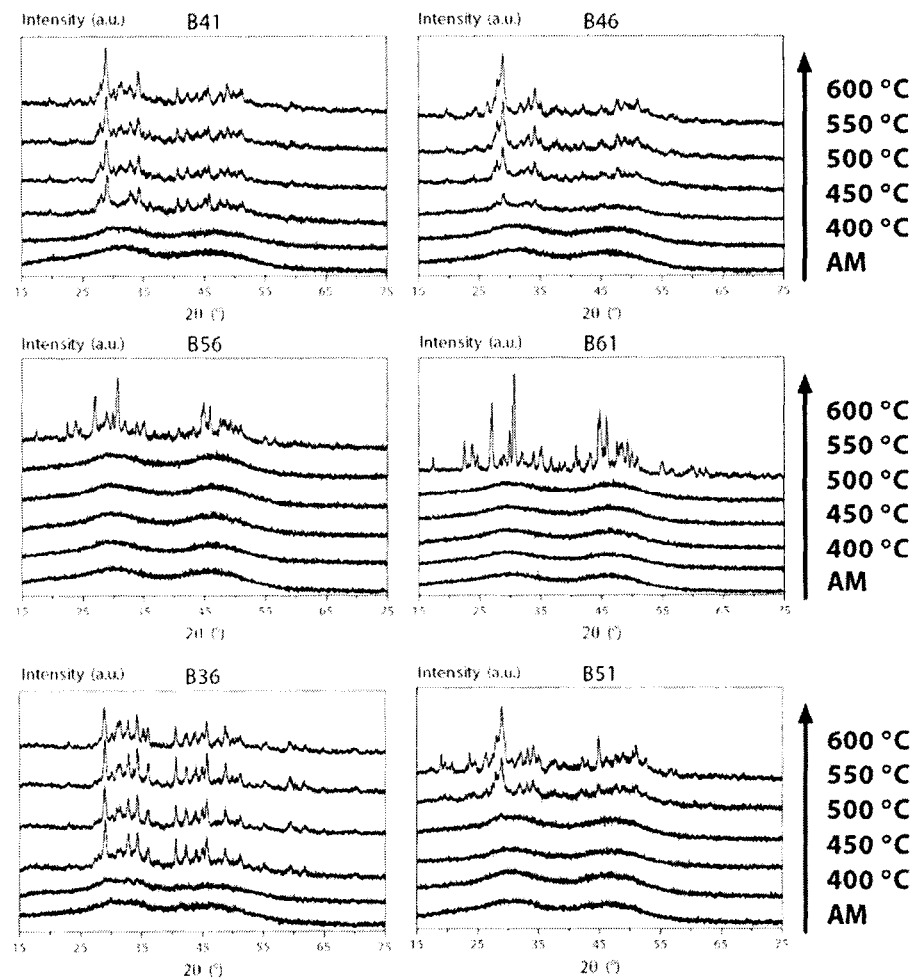
FIG. 2 shows x-ray diffraction (XRD) spectra of the biomaterials of Example 1, according to embodiments of the present disclosure.
Figure 3:
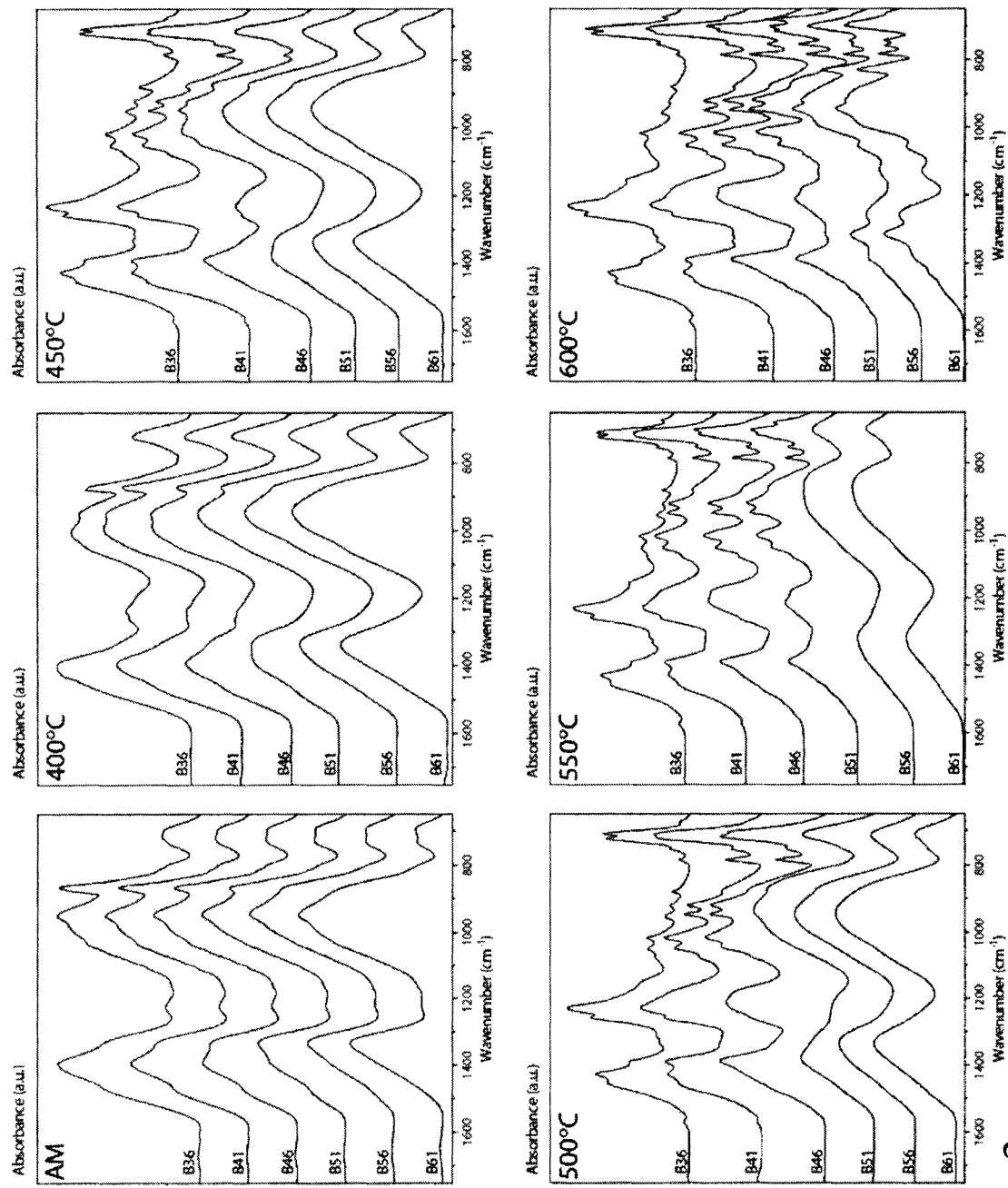
FIG. 3 shows ATR-FTIR spectra of the biomaterials of Example 1 calcined at different temperatures, according to embodiments of the present disclosure.

FIG. 2 illustrates the x-ray diffraction spectra for the compositions of Table 1. All the biomaterials of Example 1 were amorphous at a 400° C. calcination temperature which suggests homogeneity. Progressive crystallization was observed with increasing calcination temperature, with low borate content glasses crystallizing at lower temperatures. The lower boron containing formulations began to crystallize before 450° C. The as-made glass particles displayed two broad humps indicating their amorphous and homogenous nature except for B36 which displayed a number of minor peaks, attributable to a precipitate phase. At 600° C. all Example 1 compositions were crystallized into various sodium calcium borates verified by XRD and FTIR, indicating the successful incorporation of the precursors into the glass network during the sol-gel processing (FIG. 3). It was also found that the compositions with higher sodium content tended to crystallize at lower temperatures, which was corroborated by ATR-FTIR spectroscopy which showed sharp, doublet peaks at increased calcination temperatures, indicating crystallization. Since all Example 1 compositions remained amorphous post calcinations at 400° C., and amorphous materials tend to be more bioactive, compositions calcined at 400° C. were chosen to compare the properties of the various Example 1 glasses.

Example 4

Thermal Analysis

Differential scanning calorimetry (DSC) (Jupiter STA 449™) was performed using 30 mg of calcined glass powder in a Pt crucible under flowing argon purge. Analysis was carried out between 50 and 1000° C. at a heating rate of 10° C./min, followed by furnace cooling to room temperature. The output was used to calculate glass transition and crystallization temperatures ($T_g$ and $T_c$, respectively), which are presented in Table 3.

TABLE 3

Glass transition temperature ($T_g$) and crystallization temperature ($T_c$) of embodiments of biomaterials according to present disclosure (B36, B41, B46, B51, B56 and B61) and comparative example 45B5

| ID | $T_g$ (° C.) | $T_c$ (° C.) |
|---|---|---|
| B36 | 431 | 474 |
| B41 | 441 | 510 |
| B46 | 453 | 525 |
| B51 | 474 | 579 |
| B56 | 485 | 632 |
| B61 | 484 | 639 |
| Comparative Example 45B5 | 473 | 531 |

An increase in both $T_g$ and $T_c$ was observed with increasing in glass borate content. The DSC also corroborated the crystallization behavior observed through XRD in Example 3.

Example 5

Textural Particle Properties

The sieved particle sizes and porosities of the sol-gel glass compositions of Example 1 (all calcined at 400° C.) were compared to those of the comparative melt-derived glass particles of Example 2. Particle sizes ($D_{50}$) were determined using a sedigraph (Horiba LA-920™). The specific surface areas of the calcined powders (400° C., n=3) were measured with $N_2$ (g) adsorption and desorption isotherms collected with a Micrometics TriStar 3000™ (Micromeritics Instrument Corporation, Norcross, Ga.) gas sorption system. The specific surface areas were determined from the isotherm with the BrunauerEmmettTeller (BET) method (S. Brunauer, P. H. Emmett, E. Teller, Adsorption of gases in multimolecular layers. *Journal of the American Chemical Society* 60, 309-319 (1938)). The average pore width and pore volume was provided using the adsorption isotherms using the Barrett-Joyner-Halenda (BJH) method (L. G. Joyner, E. P. Barrett, R. Skold, The Determination of Pore Volume and Area Distributions in Porous Substances. II. Comparison between Nitrogen Isotherm and Mercury Porosimeter Methods. *Journal of the American Chemical Society* 73, 3155-3158 (1951); published online Epub1951/07/01 (10.1021/ja01151a046)). The results are presented in Table 4.

TABLE 4

Textural particle properties of embodiments of biomaterials according to present disclosure (B36, B41, B46, B51, B56 and B61) and comparative example 45B5

| ID | D50 (μm) | SSA ($m^2/g$) | Pore Width (nm) | Pore Volume ($cm^3/g$) |
|---|---|---|---|---|
| B36 | 34.7 | 54.9 ± 7.7 | 32.8 ± 2.0 | 0.42 ± 0.06 |
| B41 | 34.6 | 71.8 ± 8.3 | 33.2 ± 1.9 | 0.65 ± 0.11 |
| B46 | 43.8 | 93.8 ± 8.2 | 28.9 ± 0.7 | 0.74 ± 0.05 |
| B51 | 33.7 | 114.2 ± 14.9 | 32.9 ± 1.0 | 0.94 ± 0.18 |
| B56 | 38.8 | 121.0 ± 12.9 | 29.6 ± 0.4 | 0.98 ± 0.11 |
| B61 | 47.1 | 138.4 ± 11.8 | 29.0 ± 0.7 | 1.18 ± 0.12 |
| Comparative Example 45B5 | 44.1 | 0.238 ± 0.017 | 34.0 ± 8.6 | 0.00089 ± 0.00006 |

As can be seen, embodiments of the biomaterials of the present dislcosure made using an embodiment of the sol-gel method of the present disclosure have specific surface area and total pore volume values much higher than the melt-derived comparative example, ~400 and ~800 times more respectively.

Furthermore, the specific surface area and total pore volume could be controlled by varying the boron concentration. SSA and pore volume increased with increasing glass borate content. Reduction in surface area is the driving force in densification and the biomaterials with the lowest boron concentrations have the lowest specific surface area and total pore volume suggesting they are the most dense. This is supported by XRD which shows that the low boron content glasses crystallize at the lowest temperatures (FIG. 2). Furthermore, this trend is not due particle size because the glass with the highest surface area also has the largest particle diameter ($D_{50}$). In contrast, the average pore width remained consistent which may be attributable to uniform processing conditions. An increase in the calcination temperature of B46 (calcination at 400° C., 450° C., 500° C., 550° C. and 600° C.) of Example 1, led to a decrease in SSA and pore volume.

Example 6

Structural Properties

Each biomaterial of Example 1 remained amorphous according to XRD and the structure was further examined by Attenuated total reflectance-Fourier transform infrared (ATR-FTIR) and Solid state $^{11}B$ nuclear magnetic resonance (NMR). For the ATR-FTIR, a Spectrum 400™ (Perkin-Elmer) was used to collect spectra in a wavenumber range between 4000 and 650 $cm^{-1}$ with a resolution of 4 $cm^{-1}$ using 64 scans per sample. All spectra were baseline corrected and normalized to the total area surface area under absorption bands using Spectrum software (Perkin-Elmer, USA). For the NMR, $^{11}B$ NMR spectra were recorded on an Agilent/Varian VNMRS300 spectrometer with a $^{11}B$ frequency of 96.2 MHz. Approximately 2000 accumulations for each spectra were obtained by applying a 90 degree pulse of microseconds every 8 seconds with proton decoupling.

The three main regions associated with borate-based glasses were present at 850-1200 $cm^{-1}$ (B—O stretching of $BO_4^-$ units), 1200-1500 $cm^{-1}$ (B—O stretching of $BO_3$ units), and a band at ~720 $cm^{-1}$ attributable to the B—O—B bending of $BO_3^{3-}$ units, which was more defined in lower borate content glasses (FIG. 3). With a decrease in glass borate content, the broad band between ~942 and ~1000 $cm^{-1}$, attributable to the B—O linkages of $BO_4^-$, formed a defined shoulder peak at ~870 $cm^{-1}$, which is characteristic of the B—O stretching of boroxoal rings as observed in the B36 to B51 range of the Example 1 glasses. A comparison of the spectra of 45B5 (Comparative Example 2) and B46 (Example 1) indicated that both glasses were of analogous structures as they displayed similar peaks. In FIG. 3 it can be seen that as the calcining temperature increases the glasses become more crystalline as seen by the sharp peaks on the XRD diffractograms. Lower borate containing glasses crystallize first likely due to their poorly connected glass network which allows for quicker densification.

Figure 4:
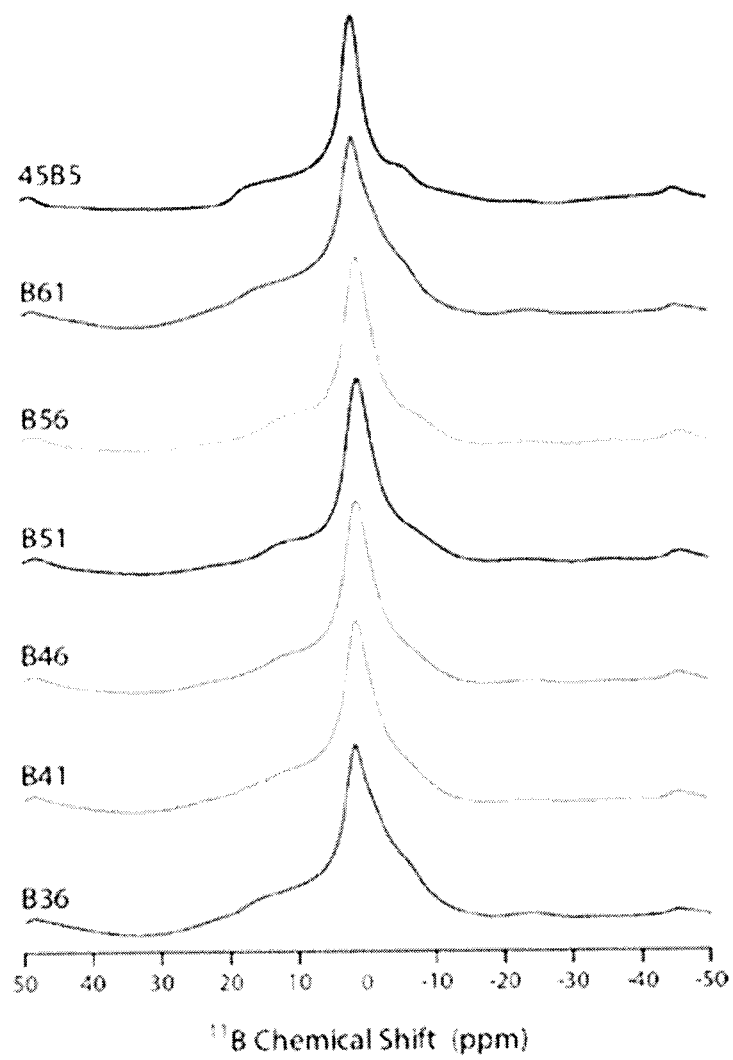
FIG. 4 shows NMR spectra of the biomaterials of Example 1, according to embodiments of the present disclosure.

$^{11}B$ MAS NMR spectroscopy (FIG. 4) provided geometrical information on borate unit of the biomaterials of Examples 1 and 2. All biomaterials exhibited a large, fairly sharp peak near 0 ppm which can be attributed to $^{11}B$ nuclei occupying a fairly symmetric site in chemical structure. The small broadening to the right of this peak, as seen in B46-B61, may be due to $^{11}B$ in less symmetric sites. B36, B41 and B61 showed greater broadening on the left side which may indicate $^{11}B$ in asymmetric sites (i.e. $BO_3$) or the same amount but in sites of less symmetry. The resonance associated with $BO_4$ was quite narrow located in a chemical shift range of 0 and −11 ppm due to its small quadrupole coupling constant. Conversely, $BO_3$ had a stronger quadropole interaction and produced a more broad resonance between 14 and 18 ppm. Further, when $^{11}B$ occupies a state of low symmetry, the relaxation times are relatively short (100 ms) due to its quadrupolar nucleus. The glasses analyzed in this study required an 8 second delay between pulses suggesting the $^{11}B$ were in a state of high symmetry and likely tetrahedrally coordinated, supporting the ATR-FTIR spectra.

Example 7

Calculation of Glass Network Connectivity

Network connectivity ($N_C$) is a measure of the bridging oxygen bonds per network former (usually calculated for an Si atom in silicate-based glasses) and has been used to predict the bioactivity of glasses. $N_C$ is measured on a scale of 0 to 4, with 4 indicating a fully connected, chemically most stable network (e.g., quartz). On the other hand, glasses with an $N_C$ between 2 and 2.6 have generally been regarded as bioactive (e.g. Edén M. Journal of Non-Crystalline Solids. 2011; 357:1595-602), e.g., Bioglass® (45S5), which has an $N_C$ of 2.12 (Hill R G et al Journal of Non-Crystalline Solids. 2011; 357:3884-7) as calculated using Equation (1).

$$N_C = \frac{4(SiO_2) - 2[M_2^I O + M^{II} O] + 6[P_2O_5]}{[SiO_2]} \quad (1)$$

where $M^I$ and $M^{II}$ represent glass network modifiers sodium and calcium, respectively. Modeling and NMR studies, have indicated that the phosphorous does not enter the glass network (i.e., no Si—O—P bonds are formed) and remains as an orthophosphate [$PO_4^{3-}$], which is accounted for in the above calculation. However, Si—O—P bonds can occur at higher P concentrations (>50 mol %) [8].

Figures 5, 6:
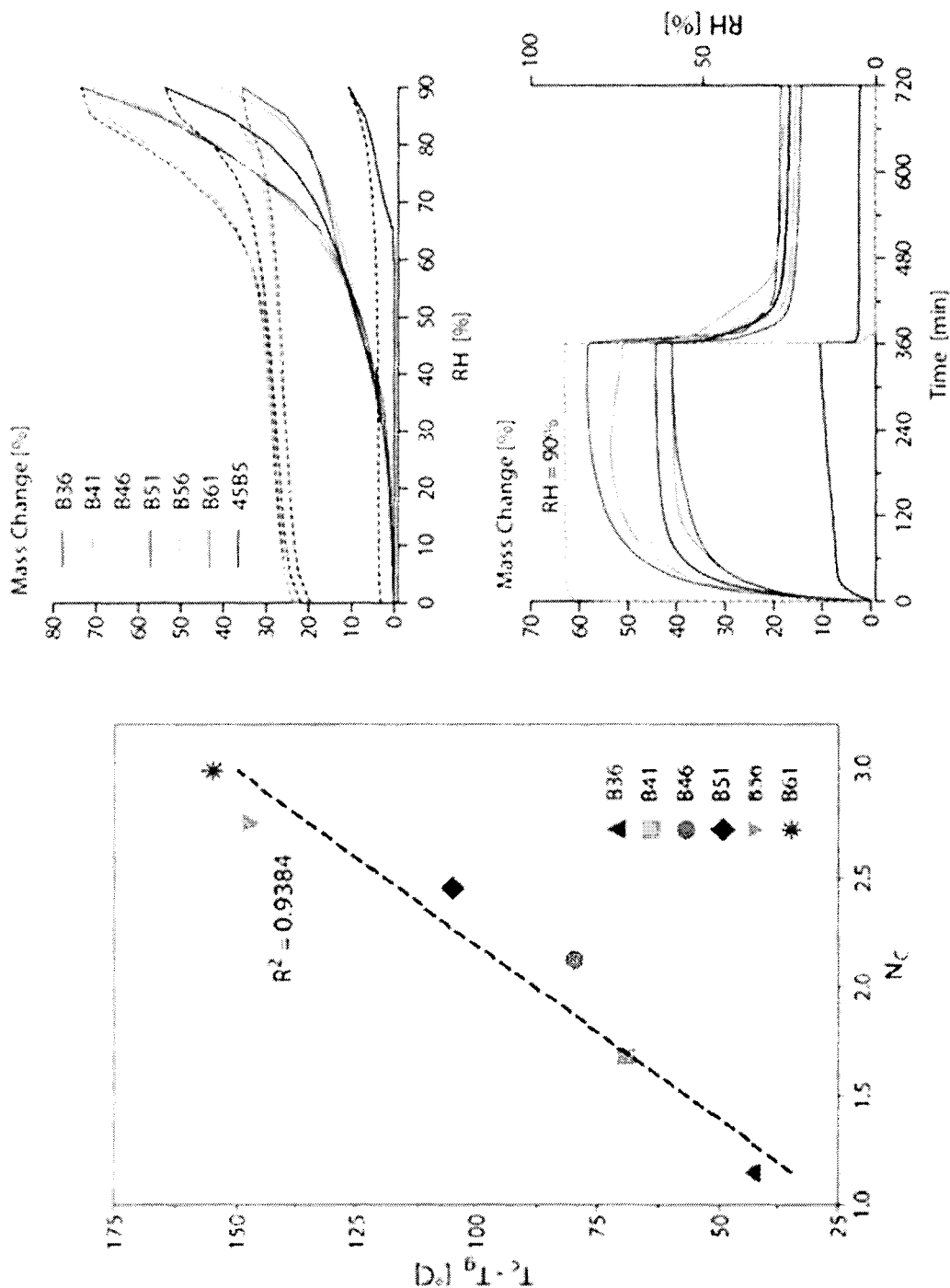
FIG. 5 shows relationship between crystallization temperature ($T_c$), glass transition temperature ($T_g$) and $N_C$ for the biomaterials of Example 1, according to embodiments of the present disclosure.
FIG. 6 shows Dynamic Vapour Sorption (DVS) for the biomaterials of Example 1, according to embodiments of the present disclosure.

In the case of borate-based glasses, while it is also possible to form B—O—P bonds, as in the case of silicate-based glasses, it is assumed that the phosphorous does not enter the glass network and is present in an orthophosphate. In addition, if it is assumed that boron is 4-coordinted, as supported by the ATR-FTIR and NMR data, then a similar $N_C$ value can be calculated as that for Bioglass®. However, it should be noted that there are three main limitations to using this approach with sol-gel derived glasses, where: 1) The above calculation does not take into account the increased surface area and porosity; 2) not all boron is 4-coordinated; and 3) the sol-gel process results in residual OH$^-$ groups on the surface, which may contribute to the bioactivity rates of the SGBGs in this study, even in $N_C$ ranges where bioactivity is thought to be inhibited. The latter, has been previously demonstrated for sol-gel derived silicate-based glasses. A plot (FIG. 5) of the relationship between $N_C$ and the difference between $T_c$ and $T_g$ of each glass composition of Example 1, demonstrated a linear correlation ($R^2$=0.9384; FIG. 5). An increase in the difference between $T_c$ and $T_g$ provides a good estimate of the tendency of the glass to remain amorphous, which can be used to predict the glass forming ability of the compositions of Example 1. As verified by XRD and ATR-FTIR (FIGS. 2 and 3, respectively), glasses with higher borate content remained amorphous at higher calcination temperatures and suggested that these compositions favored glass formation.

Example 8

Reactivity: Vapour Sorption of the Glasses

Under controlled temperature and humidity, vapour sorption of the biomaterials of Examples 1 and 2 was examined using a DVS Intrinsic (Surface Measurements Systems Ltd.) measuring mass changes (±0.1 μg). This may be an indicator of their potential solubility and reactivity. Approximately 5 mg of the glass particles from Examples 1 and 2 were placed in an aluminum pan and inserted into a chamber kept at 37±0.05° C. Two methods of analysis were carried out: 1) the relative humidity (RH) was increased stepwise at 5% RH up to 90% RH then back down to 0% RH while the relative mass change was measured when equilibrium was reached or after maximum of 4 h; 2) the glass particles were directly exposed to 90% RH for 6 h, which was then reduced back down to 0% RH for another 6 h.

As seen in FIG. 6, mass changes for all biomaterials of Example 1 were similar up to 60% RH and increased significantly until 90% RH. The % mass change at 90% RH correlated to the formulation with the lowest borate content, B36, having the greatest percent mass change (~74%) compared to B61 (~36%). Upon decreasing RH, desorption mainly occurred between 90 and 55% RH for the lower borate content glasses. The final mass change at 0% RH ranged between 19.5 and 23.7% and correlated with glass composition.

In contrast, the comparative glass of Example 2 did not indicate mass change until approximately 65% RH, where it gradually increased to ~11% at 90% RH, while the biomaterials of Example 1 began to change at as little as 5% RH. Desorption in the comparative glass of Example 2 mainly occurred between 90 and 65% RH reaching a final mass change of ~3%.

Upon the direct exposure to 90% RH for 6 hours, the biomaterial glasses of Example 1 experienced an immediate rapid increase in % mass change within the first 2 h, and followed by a slower rate of increase up to 6 h. The rate and extent of % mass change (~58 to ~41%) were dependent on the glass composition and increased with a decrease in glass borate content suggesting greater extent of bioactivity. Upon lowering the RH to 0%, the mass change % rapidly decreased with lower borate content glasses indicating greater extent of final % mass change. For the comparative glass of Example 2, its direct exposure to 90% RH resulted in ~11% mass change at 6 h, which was less than that of the sol-gel equivalent (B46 of Example 2) (~48%). In addition, beyond the first 2 h, 45B5 of Example 2 underwent a linear % mass change, similar to that experienced by melt-derived silicate and phosphate-based glasses.

Therefore, reactivity, as indicated by vapour sorption, was found to be highly dependent on SGBG composition, where atomic and molecular structures play prominent roles in the chemical durability of multi-component glasses and can be related to $N_C$. It is likely that in the case of lower borate content glasses, the fewer boron units resulted in more terminal groups, specifically OH$^-$, which were more prone to aqueous interaction and resulted in higher extents of mass change. This is particularly relevant to sol-gel derived glasses as these terminal groups are not fully removed during drying and calcination. On the other hand, the role of SGBG textural properties (SSA and pore volume) were prominent as B46 and 45B5 experienced drastically different % mass changes. While DVS is mainly used in the pharmaceutical and food science fields it has recently been used to measure the reactivity of bioactive phosphate glasses. This technique has shown to correlate well with weight loss measurements and since it is difficult to obtain accurate weight loss measurements with nano porous powders, the DVS serves as good substitute to examine aqueous reactivity.

Example 9

Reactivity: Ion Release

Ion release of B, Ca, Na, and P from the biomaterials of Example 1 compared to the glass of Example 2 in deionized water (DIW) at a 1.5 mg/mL ratio, were quantified using an inductively coupled plasma optical emission spectrophotometer (ICP-OES) (Thermo Scientific iCAP 6500). 10 mL aliquots were filtered through a 0.2 μm nylon filter and stored in a 15 mL falcon tube to which 4% (w/v) nitric acid (Fisher Scientific, CAN) was added. NIST standards were used as calibration values. The pH of the DIW solution was measured at each time point using an Accumet XL20 pH meter (Fisher Scientific).

Figure 7:
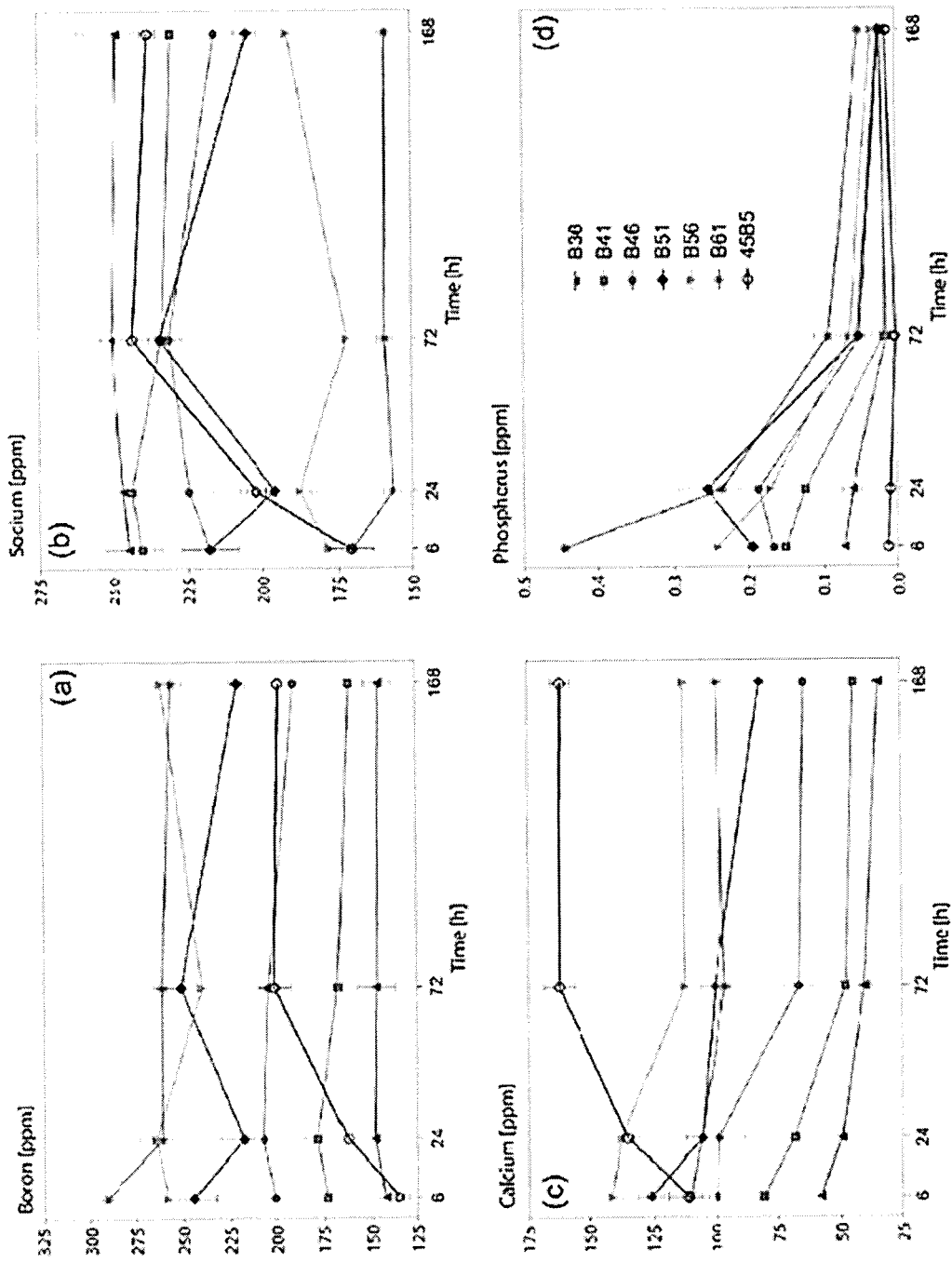
FIG. 7 shows release of (a) boron, (b) calcium, (c) sodium and (d) phosphorus ions from the biomaterials of Example 1, according to embodiments of the present disclosure, and the comparative biomaterial of Example 2, as a function of time in distilled water.

ICP-OES measurements up to day 7 in DIW revealed the release of all four SGBG components (FIG. 7). There were rapid rates of release of boron and sodium ions, which were dependent on borate and soda contents in the Example 1 glasses, respectively. Beyond the 6 h time point, boron and sodium ion concentrations remained constant, indicating their full release. While the release rates of calcium and phosphorous ions were also rapid within the first 6 h, the extents of the release of these ions were inversely related to glass composition. Beyond the 6 h time point, there was a concomitant decrease in the concentrations of these ions in solution that was possibly due to their complexing. The rates of ion release from the Example 1 glass compositions were supported by changes in DIW pH, rapidly increasing within the first 6 h, then stabilising at a constant value, which suggested full ion release. The increase in pH values corresponded with glass composition, where glasses with lower borate content (i.e., higher soda content) resulted in greater extents of pH increase. For all Example 1 compositions, the starting pH was about 5.5 and had risen steeply by 6 h. For B36, the pH rose sharply to about 10, for B41 to about 9.6, for B46 to about 9.3, for B51 to about 9.1, for B56 to about 9.0, for B61 to about 8.8.

The ion release profiles from the Example 1 glasses were distinct from those of the comparative melt-derived glass of Example 2 (45B5), which demonstrated a slower, more gradual release rate, where by day 3, the concentration of boron ions in solution reached a similar level to that of B46 achieved after 6 h. Sodium ion release was also higher in 45B5, which may be due to the lower release of boron ions, leading to a more basic solution. The higher extent of sodium ion release resulted in higher pH values, even with the significantly lower textural properties of the melt-derived 45B5 (pH rising from about 5.5 to about 10.5 at 6 h. Furthermore, the release of calcium ions from 45B5 displayed a contrasting trend to that of B46, where after the 6 h time point, it steadily increased in concentration that eventually stabilized at day 3. The extent of phosphorous ion release from 45B5 was found to be at least 10-fold lower when compared to B46.

It is believed that the rate of calcium and phosphorus release from the biomaterial influences the rate and/or extent of mineralization.

Example 10

Bioactivity—In Vitro Mineralization

The extent of mineralization of the biomaterials of Example 1, calcined at 400° C., and the glass of Example 2, using Kokubo's simulated body fluid (SBF) (pH 7.4) was investigated. The use of SBF to examine bioactivity is regarded as the standard method to examine acellular mineralization. Glass powder was added to sterile 50 mL falcon tubes containing SBF at a 1.5 mg/mL ratio and stored in an oven at 37° C.±1° C. Twice per day, the vials were gently agitated in order to reduce agglomeration of the particles. Mineralization of the glasses was examined at the end of 6 h, 1 d, 3 d, and 7 d time points when the powders were gently rinsed twice with DIW then twice with ethanol, dried overnight at room temperature, and then dried in an oven for 1 d at 60° C. At each time point the pH of the SBF solution was measured using an Accumet XL20 pH meter (Fisher Scientific).

In a parallel study on the biomaterials of Example 1, to further examine in vitro mineralization, a 0.02M $K_2HPO_4$ solution, adjusted to pH 7 using dilute HCl was used for the same procedure as the SBF. This solution has commonly been used to investigate acellular mineralization of borate based glasses (A. Yao et al, *J. American Ceramic Society* 90, 303-306 (2007); W. Huang et al. *J. Materials Science: Materials in Medicine* 17, 583-596 (2006)).

Figure 8:
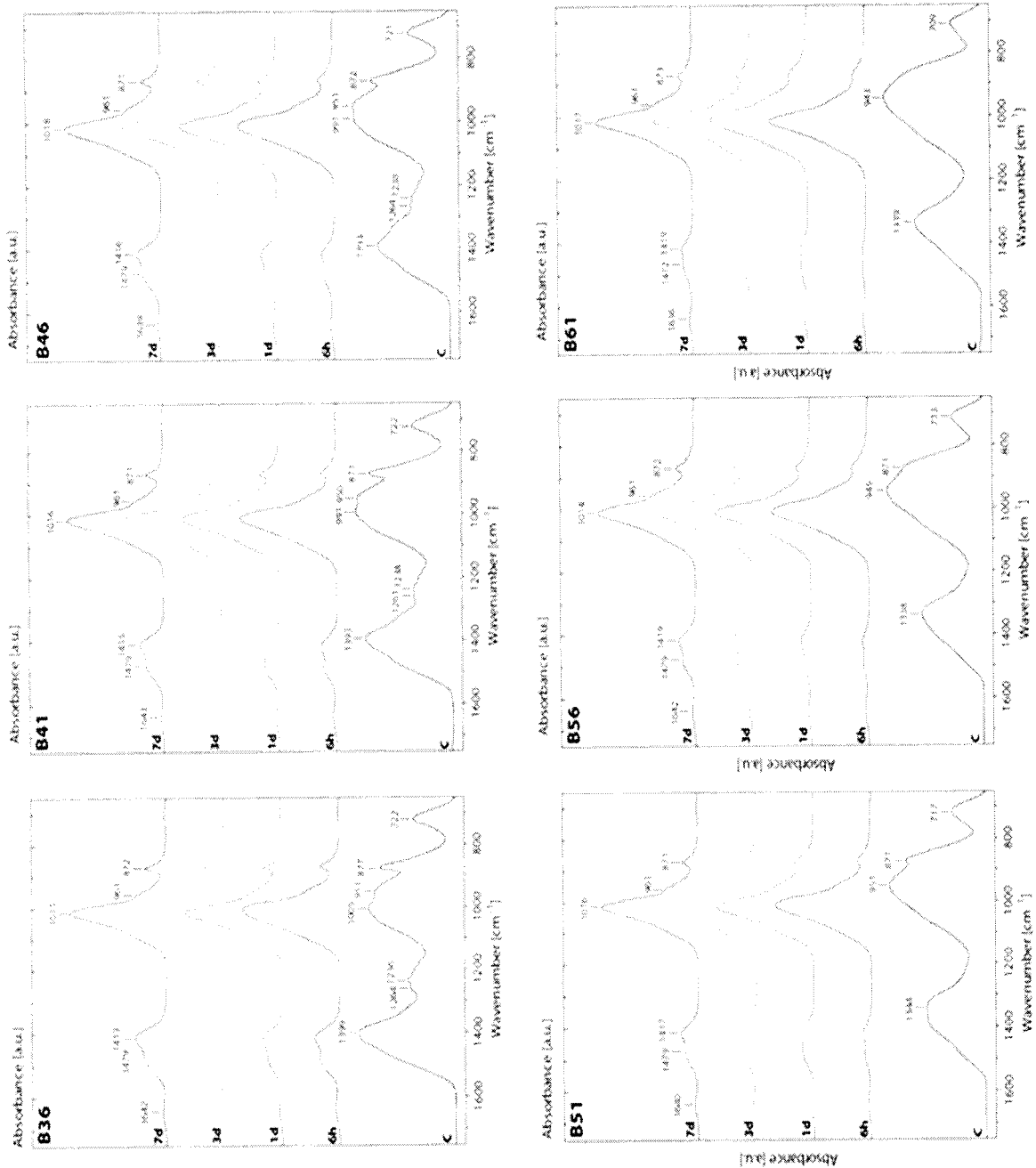
FIG. 8 shows ATR-FTIR spectra of the biomaterials of Example 1 at different time points after immersion in simulated body fluids (SBF), according to embodiments of the present disclosure.

ATR-FTIR confirmed carbonated-apatite was initiated after immersion in SBF for as little as 6 hours (FIG. 8). The strong band at ~1018 cm$^{-1}$ along with shoulders at 961 and 1062 cm$^{-1}$, are characteristic of the bending modes v1 and v3 of $PO_4^{3-}$ respectively. The broad bands at ~1470 cm$^{-1}$ and ~1421 cm$^{-1}$ are characteristic of the stretching mode (v1) and (v3) of $CO_3^{2-}$ respectively. The weak band at 1640 cm$^{-1}$ is due to the bending mode (v2) of water. The sharp peak at ~870 cm$^{-1}$ indicates the bending mode (v2) of $CO_3^{2-}$ as traditionally seen in carbonated apatites. However this peak was also observed in the as made compositions of Example 1, particularly in lower borate content glasses, as the B—O stretching of boroxol rings suggesting a combination of both structural forms. An increase in exposure time to SBF corresponded with these peaks becoming sharper and more defined, indicating the progressive crystallization of HCA. While higher borate containing SGBGs presented more defined phosphate peaks at earlier time points, the spectra at day 7 indicated smaller carbonate peaks.

Figure 9:
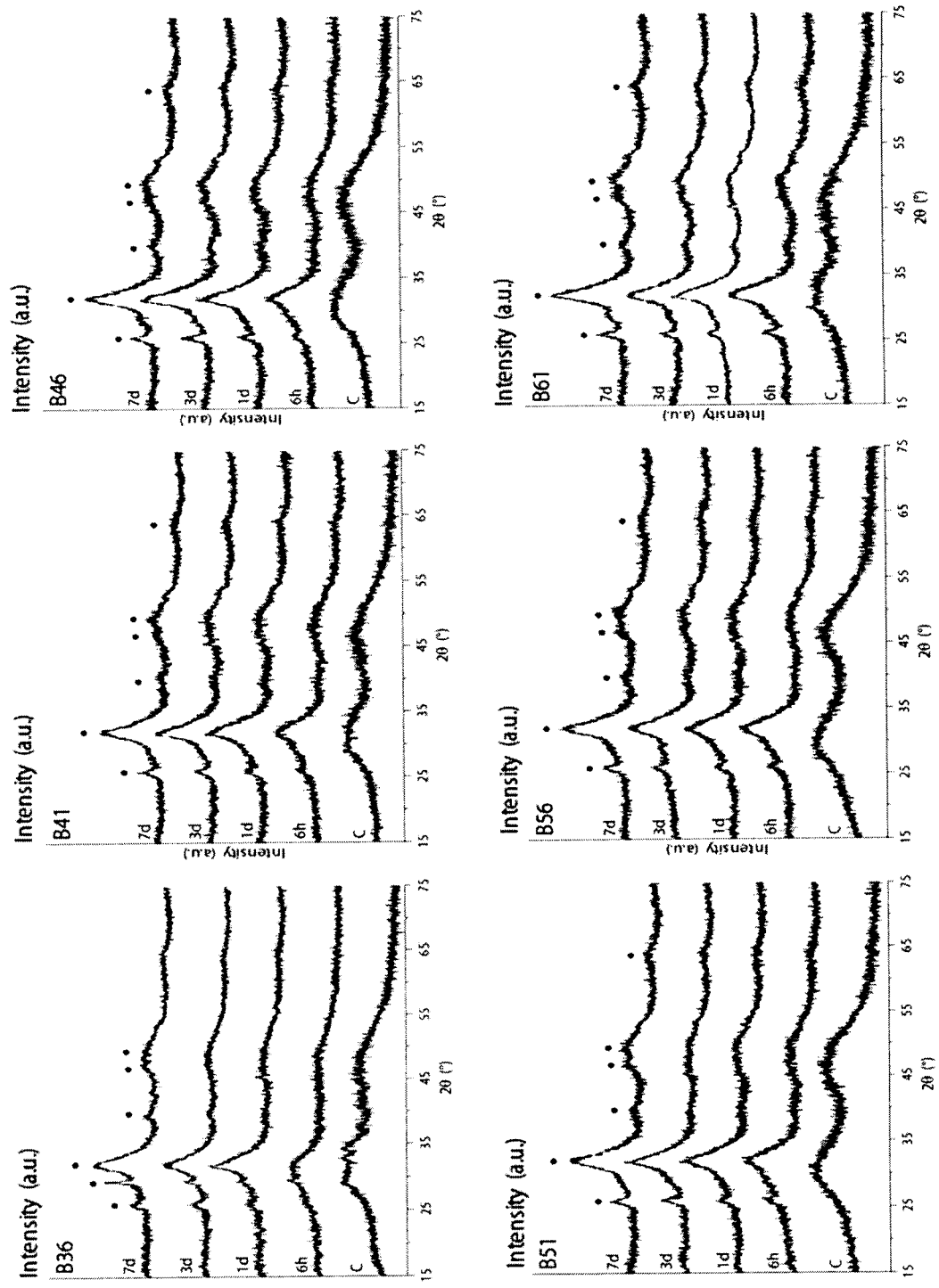
FIG. 9 shows XRD spectra of the biomaterials of Example 1 at different time points after immersion in simulated body fluids (SBF), according to embodiments of the present disclosure.

XRD analysis further confirmed apatite formation in all Example 1 glasses (FIG. 9) in 6 h as indicated by the appearance of peaks at ~25 and ~32° 2θ which are characteristic of hydroxyapatite formation (Joint Committee on Powder Diffraction Standards (JCPDS) 09-0432) where higher borate content glasses indicated more defined peaks. The peaks became more defined with time suggesting increased bone mineral formation. At day 1 all compositions showed more prominent broad hydroxycarbonate apatite (HCA) peaks, which may indicate nanosized or not fully crystallized HA. On the other hand, B36 showed the formation of a calcite phase ("☐", JCPDS 5-0586), attributable to its higher lime content, along with the lower $N_C$ likely resulting in calcite forming terminal groups. Furthermore, and in line with that observed in DIW, the increase in the pH of SBF solution corresponded with glass borate content, which favours HCA formation (FIG. 9). Without being limited to theory, the conversion mechanism of borate-based glasses to hydroxyapatite is thought to be similar to that of Bioglass® 45S5, but without the formation of an $SiO_2$ rich layer. It is thought that in the case of borate-based glasses, an HCA is initially formed on the outer glass surface which then continually reacts towards its center, causing a reduction in volume, until full conversion has taken place. This has been attributed to the relatively rapid release of $BO_3^{3-}$ and $Na^1$ ions, while the remaining $Ca^{2+}$ and $PO_4^{3-}$ ions from the glass migrate to the surface and react with similar ions in the SBF solution leading to formation of an amorphous calcium-phosphate layer that eventually crystallizes into HCA. With the SGBG formulations investigated in this study, it is proposed that a similar mechanism of conversion occurs, yet at a significantly more rapid rate compared to melt-derived glasses, attributable possibly to their significantly higher textural properties and rapid ion release rates. Therefore, in order to further examine the effect of sol-gel processing on the bioactivity of borate-based glasses, the rates of mineralization of B46 and 45B5 were directly compared.

Figure 10:
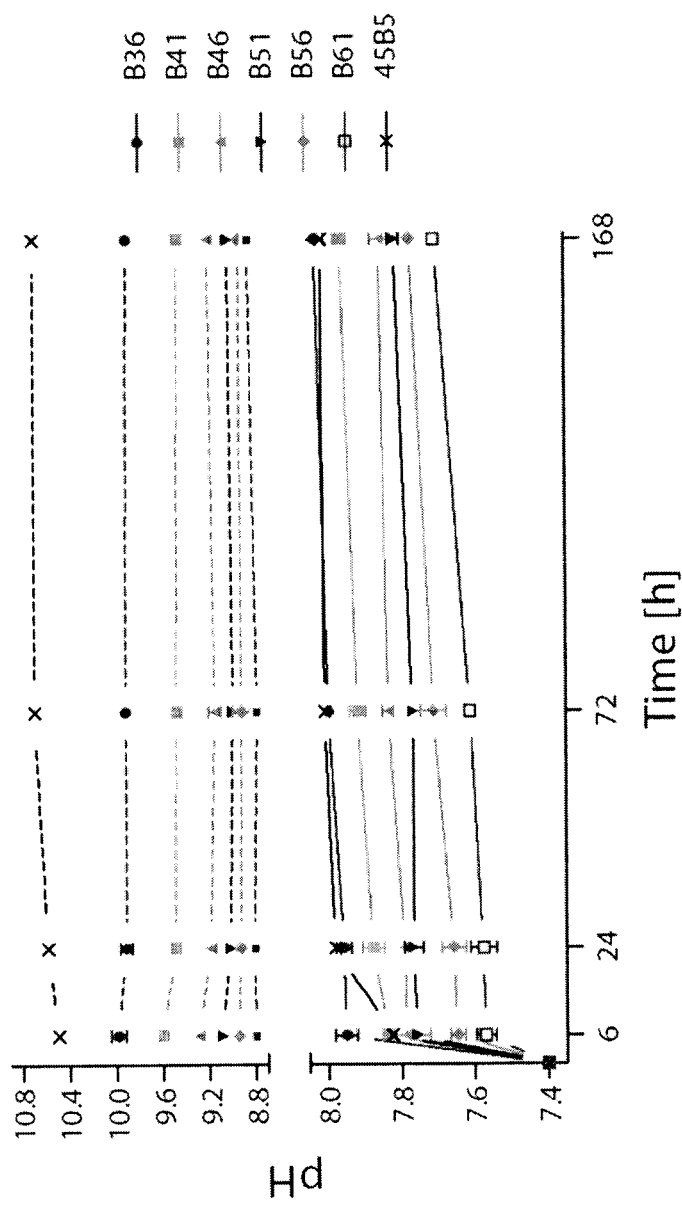
FIG. 10 shows the change in pH over dissolution time in SBF (solid line) and deionized water (DIW) (dashed line) of the biomaterials of Example 1, according to different embodiments of the present disclosure, and the comparative biomaterial of Example 2.

Increased pH of the mineralization media over time can also be a good indicator of HA formation. For all the formulations tested, the pH of the solution (SBF, DIW) increased (FIG. 10). The solid line in FIG. 10 represents the SBF data and the dashed line represents the deionized water data. The biomaterials of Example 1 rapidly reached their pH peak at 6 hours suggesting rapid ion exchange. Formulations with the highest Na content maintained the highest pH. The comparative melt-derived biomaterial of the same composition (Example 2) took about 7 days to reach the same pH level. This suggests that the dissolution rate of the biomaterials of the present disclosure is much more rapid than those with a lower surface area and pore volume.

The alkaline nature of the biomaterial solution precursors is thought to increase the connectivity of the glassy network and improve gelation. During processing this was observed as many of the compositions of Example 1 began to gel within 5 minutes of the final sodium addition.

The onset mineralization of all SGBG compositions occurred within 3 hours in SBF, demonstrating at least a ~25 fold increase in bioactivity rate relative to melt-derived borate-based glasses. The ability of the SGBGs to rapidly convert to bone-like HCA holds promise for the repair and augmentation of mineralized tissues.

Example 11

Scanning Electron Microscopy

Scanning electron microscopy (SEM) was used to investigate the morphological properties of the glass powders. Samples were sputter coated with Au/Pd and analysis was performed with an Inspect F50 Field Emission Scanning Electron Microscope (FEI Corporation, USA) at 10 kV. To determine conversion of HCA, Energy Dispersive Spectroscopy (EDS) using an attached EDAX and a TEAM EDS Analysis System was performed at 20 kV on 8 unique glass surface areas to determine the Ca/P ratio at the 6 h and 7 d time points.

Figure 11:
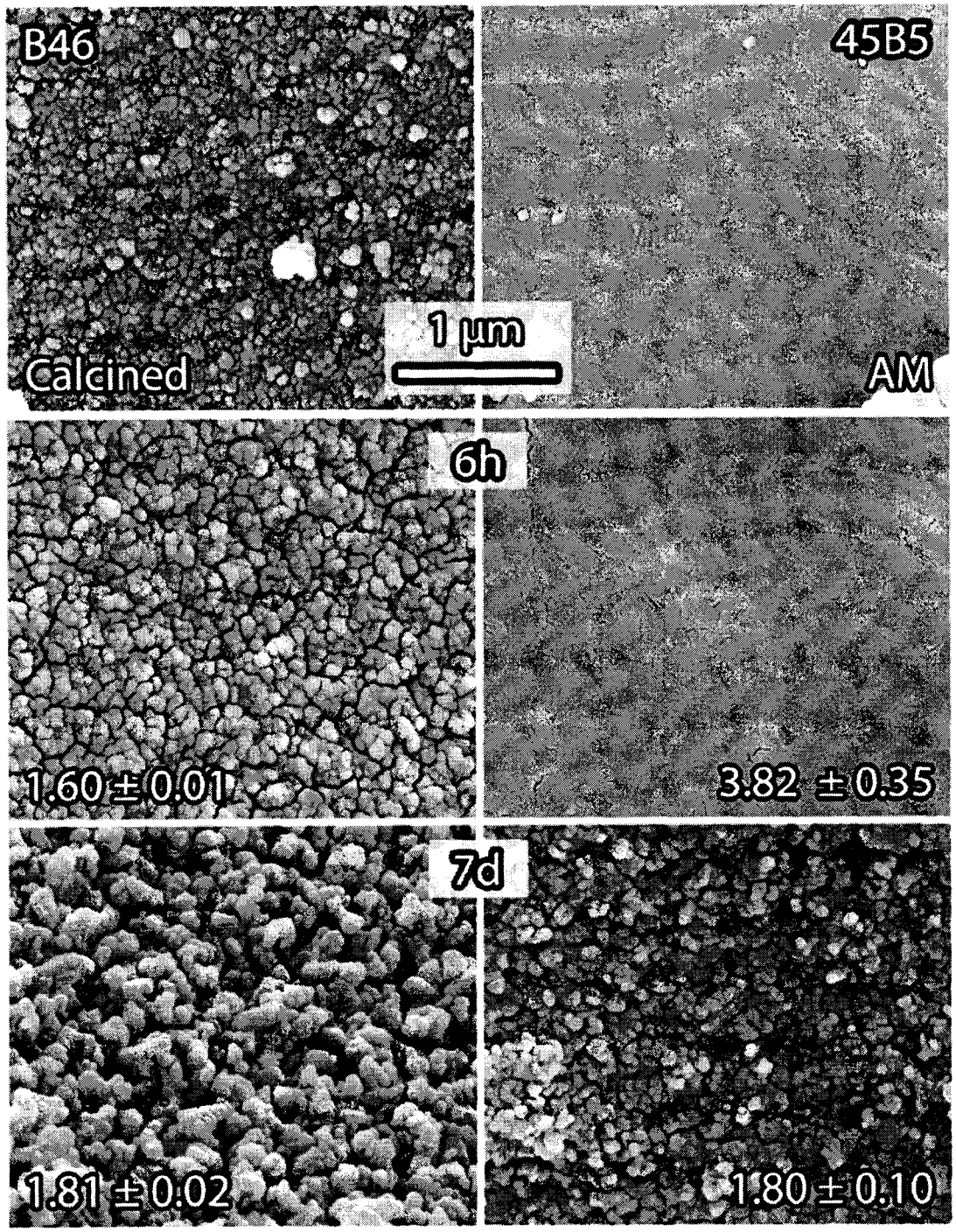
FIG. 11 shows scanning electron micrographs of the surface of (a) one of the biomaterials of Example 1 (B46) according to an embodiment of the present disclosure, and (b) the comparative biomaterial of Example 2 (45B5), after calcination, and after 6 hours and 7 days in simulated body fluids.

FIGS. 11a and 11b show SEM micrographs of B46 of Example 1 and 45B5 of comparative Example 2 at different time points: immediately after calcining, 6 hours in SBF and 7 days in SBF. The scale bar in FIG. 11 represents 10 µm and the inset scale bar represents 1 µm. Attributable to sol-gel processing, the surface of calcined B46 exhibited a rough, nanoporous texture; corroborating the textural properties in Table 4. In contrast, 45B5 displayed a relatively smooth surface appearance, typical of melt-derived glasses. However, surface roughness in both glasses became more apparent with time in SBF. EDAX analysis of B46 after 6 h in SBF indicated the rapid formation of an apatite-like calcium-phosphate layer, with a Ca/P ratio approaching that of HCA (1.60±0.01). This was in contrast to 45B5, where the Ca/P ratio at the 6 h time point was more reflective of the glass composition. However, by day 7 in SBF, a comparable Ca/P ratio was observed in both glasses. The rough porous surface of the calcined B46 becomes smoother after a 6 hour immersion in SBF possibly attributable to the washing of loose nanoparticles. However, the surfaces regained their textured appearance with time in SBF, and by day 7, the typically observed HCA morphology was apparent, which correlated with XRD and ATR-FTIR.

Figure 12:
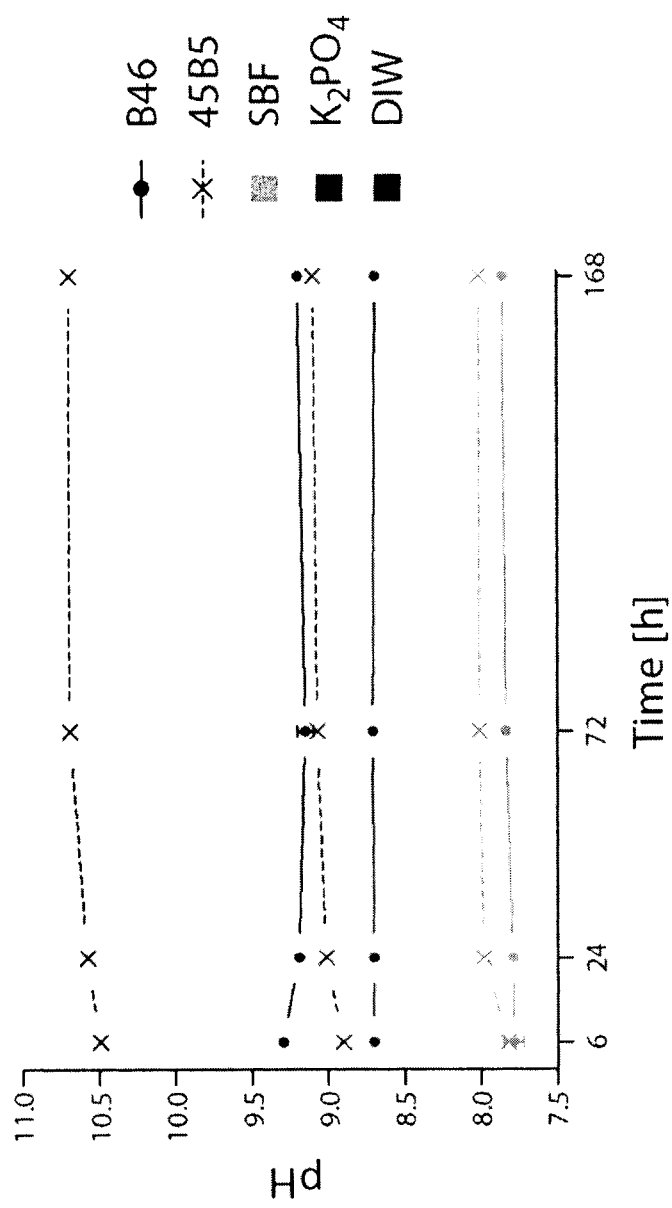
FIG. 12 shows the change in pH over dissolution time in SBF, $K_2HPO_4$ and deionized water (DIW) of one of the biomaterials of Example 1 (B46), according to an embodiment of the present disclosure, and the comparative biomaterial of Example 2 (45B5).

The pH change over time of formulation B46 of Example 1 and formulation 45B5 of Example 2 (comparative example) in three different dissolution media (deionised water (DIW); simulated body fluid (SBF); and potassium hydrogen phosphate (K2HPO4)) were investigated (FIG. 12). It was found that the melt-derived formulation of Example 2 has a higher pH than the sol-gel derived formulation of Example 1, regardless of the dissolution media.

Figure 13:
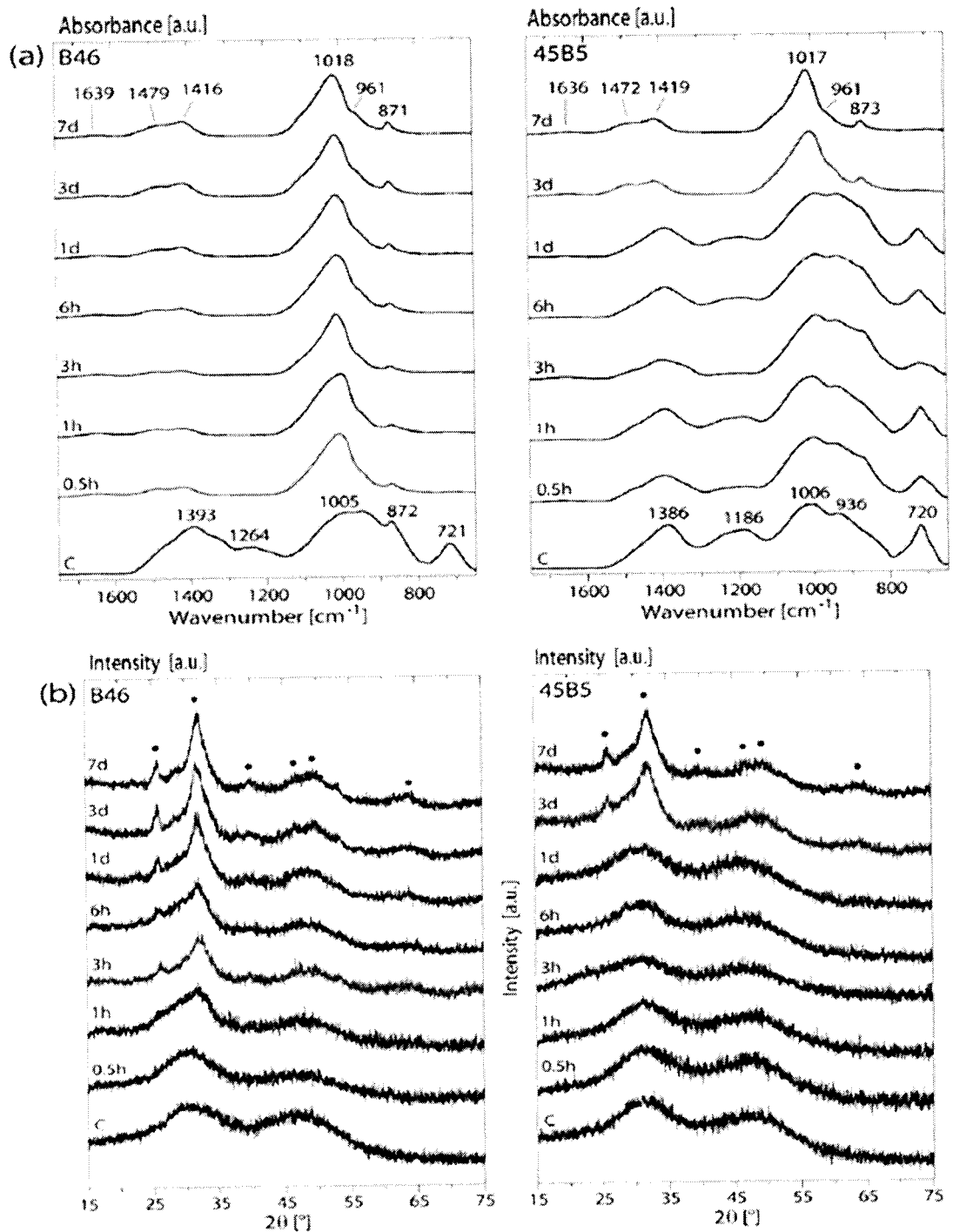
FIG. 13 are XRD spectra of one of the biomaterials of Example 1 (B46), according to an embodiment of the present disclosure, and the comparative biomaterial of Example 2 (45B5) at different time points in SBF and $K_2HPO_4$ solution.

ATR-FTIR spectroscopy of the glasses at earlier time points in SBF indicated that HCA-like formation was achieved in as little as 0.5 h in B46, compared to 3 days in the case of 45B5 (FIG. 13). Furthermore, XRD diffractograms showed that HCA formation was initiated after 3 h for B46, compared to 3 days for 45B5. This demonstration of the highly bioactive nature of the biomaterials of the present disclosure may be attributable to their ability to release greater extents of phosphate ions, thus favoring rapid HCA formation in SBF.

Figure 14:
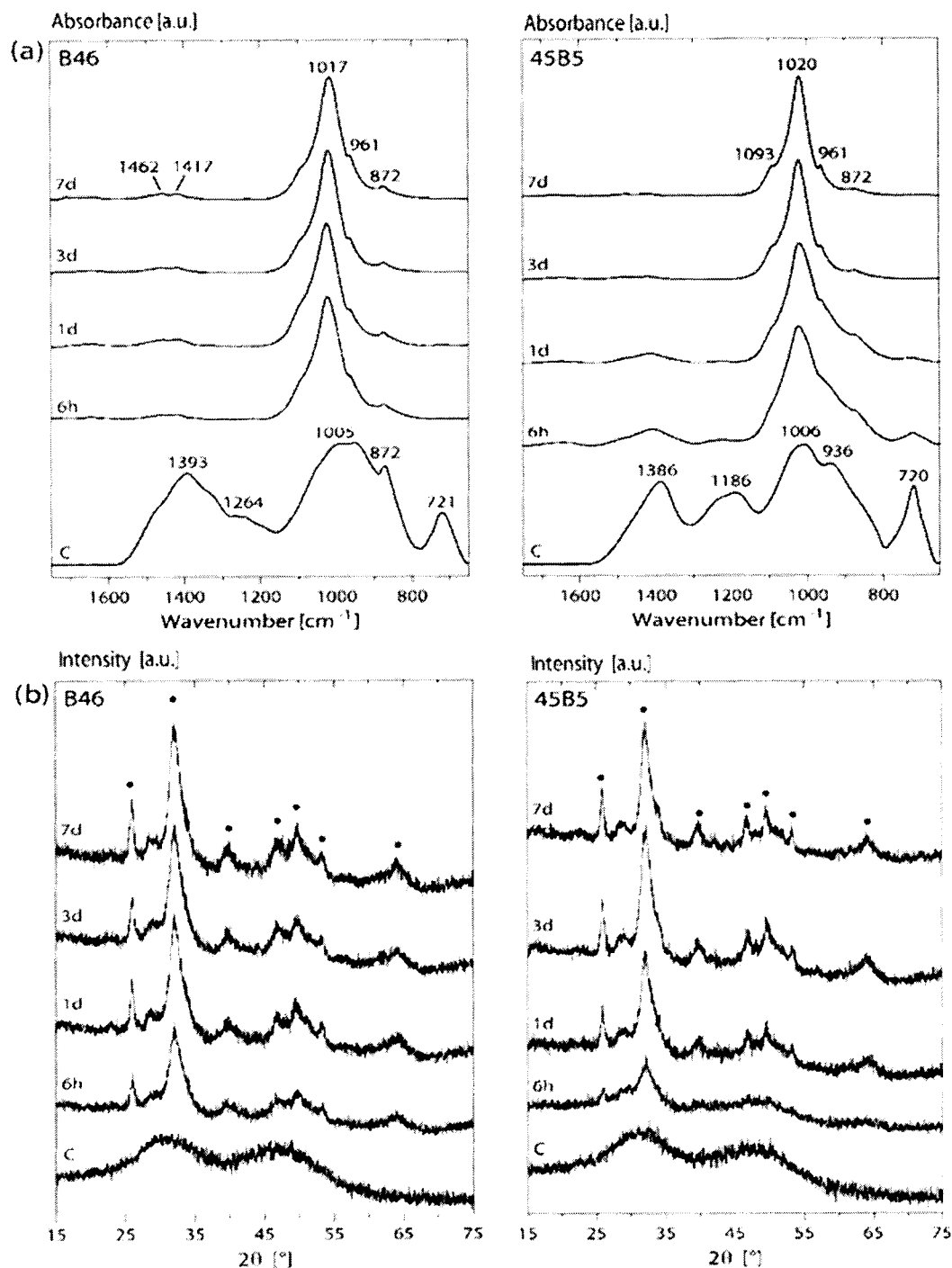
FIG. 14 are ATR-FTIR spectra of one of the biomaterials of Example 1 (B46), according to an embodiment of the present disclosure, and the comparative biomaterial of Example 2 (45B5) at different time points in SBF and $K_2HPO_4$ solution.

As a comparison to SBF, this study also investigated the mineralization of B46 and 45B5 in 0.02 M $K_2HPO_4$, which provided a 20 fold increase in phosphate content compared to SBF. It was found that apatite formation initiated within 6 h in both glasses, indicating that $K_2HPO_4$ artificially promotes rates of in vitro mineralization through the provision of excess, non-physiological concentrations of phosphate ions (FIG. 14). Furthermore, the appearance of a sharper $PO_4^{3-}$ peak and more pronounced shoulder regions in the ATR-FTIR spectra, indicated that the exposure to $K_2HPO_4$ did not favor the production of $CO_3^{2-}$ and $OH_3^{2-}$ peaks, indicators of carbonated-apatite formation. Therefore, the use of SBF in assessing in vitro bioactivity can be regarded as more representative than $K_2HPO_4$ solution.

Example 12

Calcining Temperature

Figures 15, 16:
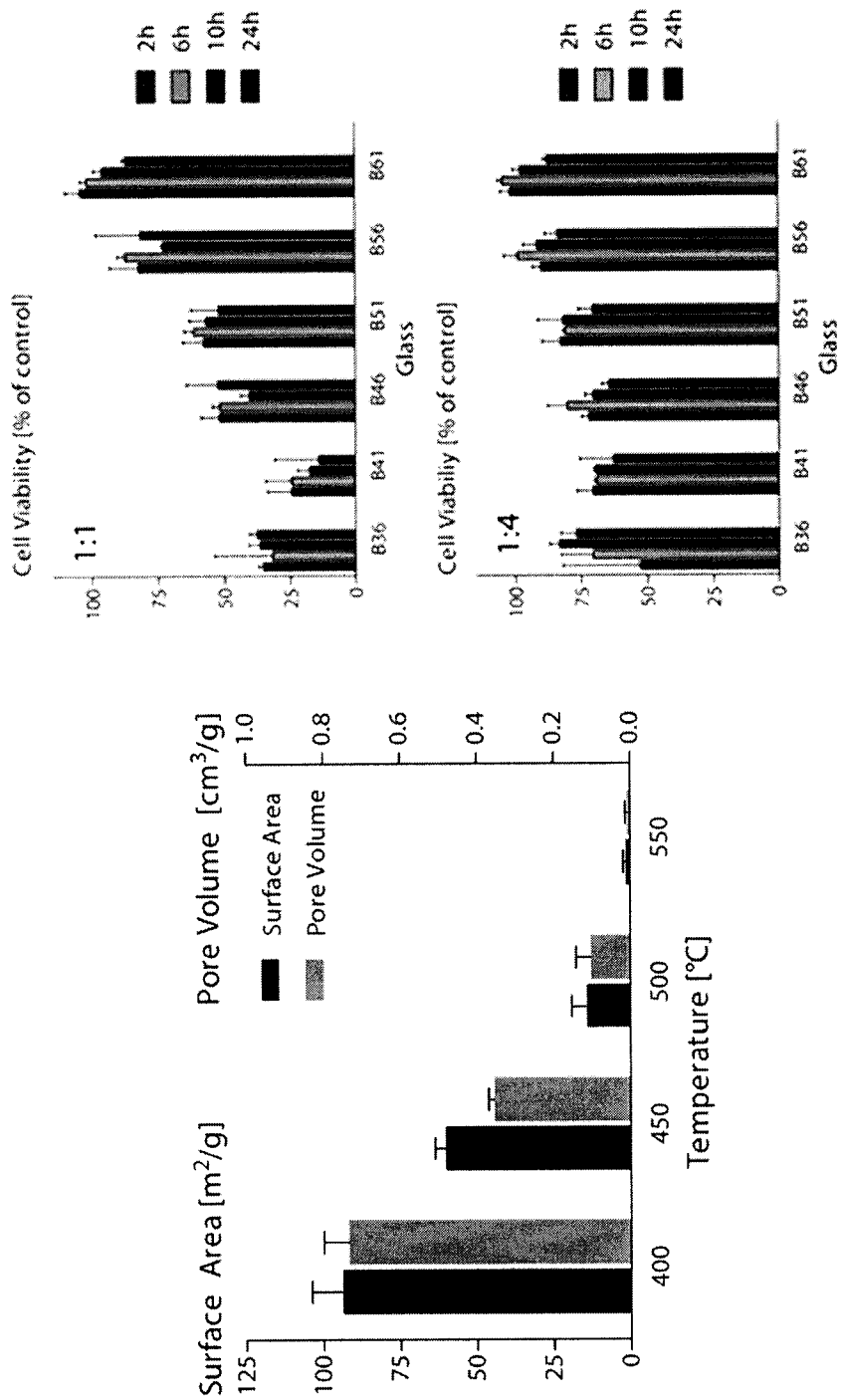
FIG. 15 is a graph showing the effect of calcination temperature on one of the biomaterials (B46) of Example 1, according to embodiments of the present disclosure, on surface area and pore volume.
FIG. 16 (a) and (b) show % mesenchymal stem cell viability in the presence of ionic release from the biomaterials of Example 1, according to embodiments of the present disclosure, at dilutions of 1:1 and 1:4 respectively.

FIG. 15 demonstrates that the porosity and surface area of the biomaterials of the present disclosure can be controlled by firing temperature during the calcination process. The biomaterials become more dense with higher firing temperatures thus diminishing their nanopores resulting in small surface areas and total pore volume. This is supported by XRD and FTIR since at these higher temperatures the glasses become crystalline. Therefore, the surface texture properties and hence the reactivity of the biomaterials of the present disclosure can be controlled by processing temperature.

Example 13

Cell Viability

Mesenchymal stem cells (MSCs) were grown to confluence in a 96 well plate. The biomaterials of Example 1 were dissolved in Dulbecco's Modified Eagle Medium (DMEM) for one day at 37 C at a 50 mg/mL ratio. Aliquots of media with dissolved ions were combined with new DMEM media at a 1:1 and 1:4 ratio then added to the cells at separate time points (2 h, 6 h, 10 h, and 24 h). The cells were then stained with Calcein-AM and fluorescence was spectroscopically read. The values were normalized to the control (wells with only media). The results (FIG. 16) showed that mesenchymal stem cells remained largely viable when in contact with the ionic release from the biomaterials of Example 1. The viability of the cells appeared to be related to composition and ionic concentration. From this it can be predicted that cellular behaviour in vivo can be controlled by controlling the dose of ionic release as well as the relative proportions of each ion.

Example 14

Borate-Glass Biomaterial without Phosphates

A three component borate-based glass biomaterial was made based on boron-sodium-calcium oxides, with borate as the sole network forming component. Specifically, the biomaterial made had the following composition: 54 wt % $B_2O_3$—22 wt % CaO—24 wt % $Na_2O$. The method here differed from that of Example 1 in that no phosphate precursor was used, and 6.53 g boric acid was dissolved in 58.33 mL 100% EtOH, followed by mixing with 25 g calcium methoxyethoxide (20%) and 11.36 g of sodium methoxide (25%). The solution was observed to have gelled within 30 minutes of adding the final precursor.

It should be appreciated that the invention is not limited to the particular embodiments described and illustrated herein but includes all modifications and variations falling within the scope of the invention as defined in the appended claims.

We claim:

1. A borate-glass biomaterial made by a sol-gel process comprising a composition having a $B_2O_3$ component, a CaO component, and at least one other component selected from a $P_2O_5$ component and a $Na_2O$ component, wherein:
    the biomaterial is silica-free;
    surface mineralization of the biomaterial, as measured by X-ray diffractometry (XRD), is initiated within 3 hours of contact with simulated body fluid; and
    the biomaterial has a surface area per mass of more than about 5 $m^2/g$.

2. The borate-glass biomaterial of claim 1, wherein the composition comprises: $aNa_2O$. $bCaO$. $cP_2O_5$. $dB_2O_3$, wherein a is from about 1-40 wt %, b is from about 10-40 wt %, c is from about 1-40 wt %, and d is from about 35-80 wt %.

3. The borate-glass biomaterial of claim 2, wherein a is from about 15-30 wt %, b is from about 15-30 wt %, c is from about 3-7 wt %, and d is from about 35-65 wt %.

4. The borate-glass biomaterial of claim 2, wherein a is from about 16-27 wt %, b is from about 16-27 wt %, c is from about 4-7 wt %, and d is from about 39-63 wt %.

5. The borate-glass biomaterial of claim 2, wherein a is about 22.9 wt %, b is about 22.9 wt %, c is about 5.6 wt %, and d is about 48.6 wt %.

6. The borate-glass biomaterial of claim 2, wherein a is about 20.7 wt %, b is about 20.7 wt %, c is about 5.1 wt %, and d is about 53.6 wt %.

7. The borate-glass biomaterial of claim 2, wherein a is about 18.4 wt %, b is about 18.4 wt %, c is about 4.6 wt %, and d is about 58.6 wt %.

8. The borate-glass biomaterial of claim 2, wherein a is about 16.2 wt %, b is about 16.2 wt %, c is about 4.1 wt %, and d is about 63.6 wt %.

9. The borate-glass biomaterial of claim 1, wherein the composition comprises: $xCaO$. $yP_2O_5$. $zB_2O_3$, wherein x is from about 5-50 wt %, y is from about 5-50 wt %, and z is from about 35-75 wt %, or x is 10-50 wt %, y is 5-35 wt % and z is 38-80 wt %.

10. The borate-glass biomaterial of claim 1, wherein the composition comprises: $lNa_2O$. $mCaO$. $nB_2O_3$ wherein l is from about 5-50 wt %, m is from about 1-50 wt %, and n is from about 40-80 wt %.

11. The borate-glass biomaterial of claim 1, wherein the biomaterial has a surface area per mass of about 5-300 $m^2/g$, 10-300 $m^2/g$, 20-300 $m^2/g$, 30-300 $m^2/g$, 40-300 $m^2/g$, 50-300 $m^2/g$, 60-300 $m^2/g$, 70-300 $m^2/g$, 80-300 $m^2/g$, 90-300 $m^2/g$, 100-300 $m^2/g$, 110-300 $m^2/g$, 120-300 $m^2/g$, 130-300 $m^2/g$, 140-300 $m^2/g$, 150-300 $m^2/g$, 200-300 $m^2/g$, 250-300 $m^2/g$, 5-250 $m^2/g$, 5-200 $m^2/g$, 5-150 $m^2/g$ or 5-100 $m^2/g$.

12. The borate-glass biomaterial of claim 1, wherein the biomaterial has a pore volume per mass of biomaterial of about 0.1-3.0 $cm^3/g$, 0.2-3.0 $cm^3/g$, 0.3-3.0 $cm^3/g$, 0.4-3.0 $cm^3/g$, 0.5-3.0 $cm^3/g$, 0.6-3.0 $cm^3/g$, 0.7-3.0 $cm^3/g$, 0.8-3.0 $cm^3/g$, 0.9-3.0 $cm^3/g$, 1.0-3.0 $cm^3/g$, 0.1-2.5 $cm^3/g$, 0.42-1.18 $cm^3/g$ or 0.1-2.0 $cm^3/g$.

13. The borate-glass biomaterial of claim 1, wherein the biomaterial can induce bone formation.

14. The borate-glass biomaterial of claim 1, wherein the biomaterial is one of amorphous, crystalline or semi-crystalline.

15. The borate-glass biomaterial of claim 1, wherein biomaterial comprises at least one of: particles, fibrils, hollow spheres, solid spheres, monoliths, fibrous form or a porous sponge scaffold.

16. The borate-glass biomaterial of claim 1, wherein the biomaterial comprises particles having a diameter of 0.2-1 μm, 5-2000 μm, 5-100 μm, or 25-75 μm.

17. The borate-glass biomaterial of claim 1, further comprising a carrier.

18. The borate-glass biomaterial of claim 1, wherein the biomaterial is coated on a bone implant surface.

19. The borate-glass biomaterial of claim 1, for use in at least one of: mineralization, reducing dentine sensitivity, bone regeneration, wound healing, filling hard or soft tissue defects, as a coating on a bone implant, for enhancing the appearance of skin, or as a drug delivery vehicle.

20. The borate-glass biomaterial of claim 1, wherein surface mineralization of the biomaterial, as measured by X-ray diffractometry (XRD), is initiated within 30 minutes of contact with simulated body fluid.

21. A method for making the borate-glass biomaterial of claim 1, comprising combining a boron precursor and a calcium precursor, with at least one of a phosphate precursor and a sodium precursor to form a mixture; gelling the mixture to form a gel; drying the gel; and calcining the dried gel, wherein the boron precursor solution is selected from trimethyl borate $B(OCH_3)_3$, triethyl borate $B(C_2H_5O)_3$, tributyl borate $B(CH_3(CH_2)_3O)_3$, Tri-tert-butyl borate ($B_3(CH_3)_3CO$) and boric acid, and wherein the calcium precursor is selected from calcium methoxyethoxide, Calcium nitrate tetrahydrate ($Ca(NO_3)_2 4H_2O$), Calcium Chloride ($CaCl_2$), Calcium Ethoxide ($Ca(C_2H_5O)_2$), and Calcium methoxide ($C_2H_6CaO_2$).

22. The method of claim 21, wherein the phosphate precursor is selected from triethyl phosphate, Trimethyl phosphate (($CH_3)_3PO_4$), Tributyl phosphate (($CH_3CH_2CH_2CH_2O)_3PO$), Dibutyl phosphate (($CH_3CH_2CH_2CH_2O)_2P(O)OH$), n-Butyl phosphate, mixture of monobutyl and dibutyl ($C_8H_{19}O_4P/C_4H_{11}O_4P$).

23. The method of claim 21, wherein the sodium precursor is selected from Sodium methoxide ($NaCH_3O$) in methanol and sodium hydroxide (NaOH).

24. The method of claim 21, wherein the mixture comprises boric acid, anhydrous ethanol, triethyl phosphate, calcium methoxyethoxide, and sodium methoxide.

25. The method of claim 21, wherein gelling the mixture comprises maintaining the solution at a temperature between about room temperature and about 60° C.

26. The method of claim 21, wherein calcining the dry gel comprises heating the dry gel to between about 400-600° C., or about 100-400° C.

27. The method of claim 25, wherein the temperature is about 37° C.

* * * * *